United States Patent
Morishita

(10) Patent No.: US 9,521,947 B2
(45) Date of Patent: Dec. 20, 2016

(54) FLUORESCENCE ENDOSCOPE APPARATUS

(75) Inventor: Koki Morishita, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 1105 days.

(21) Appl. No.: 13/611,826

(22) Filed: Sep. 12, 2012

(65) Prior Publication Data

US 2013/0006117 A1    Jan. 3, 2013

Related U.S. Application Data

(63) Continuation of application No. PCT/JP2011/055994, filed on Mar. 15, 2011.

(30) Foreign Application Priority Data

Mar. 16, 2010  (JP) ................................. 2010-059781

(51) Int. Cl.
| | | |
|---|---|---|
| A61B 5/00 | (2006.01) | |
| A61B 1/06 | (2006.01) | |
| A61B 1/00 | (2006.01) | |
| A61B 1/04 | (2006.01) | |
| G01N 21/64 | (2006.01) | |

(52) U.S. Cl.
CPC ......... *A61B 1/0638* (2013.01); *A61B 1/00009* (2013.01); *A61B 1/043* (2013.01); *A61B 5/0071* (2013.01); *A61B 5/0084* (2013.01); *G01N 21/6456* (2013.01); *G01N 2021/6421* (2013.01); *G01N 2021/6423* (2013.01); *G01N 2021/6441* (2013.01)

(58) Field of Classification Search
CPC . A61B 1/0638; A61B 5/0084; A61B 1/00009; A61B 5/0071; A61B 1/043; G01N 21/6456; G01N 2021/6423; G01N 2021/6421; G01N 2021/6441
See application file for complete search history.

(56) References Cited

U.S. PATENT DOCUMENTS

| | | | | |
|---|---|---|---|---|
| 7,426,026 | B2* | 9/2008 | Matsumoto | ........ G01N 21/6428 250/459.1 |
| 2008/0039697 | A1* | 2/2008 | Morishita | .............. A61B 1/043 600/181 |
| 2011/0282143 | A1* | 11/2011 | Matsumoto | .............. A61B 1/05 600/109 |
| 2014/0024948 | A1* | 1/2014 | Shida | ................. A61B 1/00009 600/476 |

FOREIGN PATENT DOCUMENTS

| | | |
|---|---|---|
| JP | 2005-181276 A | 7/2005 |
| JP | 2006-242899 A | 9/2006 |
| JP | 2008-128982 A | 6/2008 |
| JP | 2008-161550 A | 7/2008 |
| JP | 2009-008481 A | 1/2009 |
| WO | WO 2005/036143 A1 | 4/2005 |
| WO | WO 2007/097170 A1 | 8/2007 |
| WO | WO 2007/097171 A1 | 8/2007 |

OTHER PUBLICATIONS

International Search Report dated Apr. 26, 2011 issued in PCT/JP2011/055994.

* cited by examiner

*Primary Examiner* — Amanda Lauritzen Moher
(74) *Attorney, Agent, or Firm* — Scully, Scott, Murphy & Presser, P.C.

(57) ABSTRACT

A fluorescence-spectrum-recording unit, a fluorescence-image-acquiring unit, and a fluorescent-dye-density-calculating unit are comprised, the calculating unit calculates the densities D1 to Dm of fluorescent dyes 1 to m in each of all the pixels and in all of the pixels with the following equation, and, when there exists a pixel in which one of the calculation values of these densities is smaller than 0, a set value larger than the calculation value smaller than 0 is substituted for the density the calculation value of which is smaller than 0 in the equation, and the densities of the other fluorescent dyes are recalculated, relative to the pixel:

$$\begin{pmatrix} D1 \\ \vdots \\ Dm \end{pmatrix} = \begin{pmatrix} a1(\lambda 1) & \cdots & am(\lambda 1) \\ \vdots & \vdots & \vdots \\ a1(\lambda n) & \cdots & am(\lambda n) \end{pmatrix}^{-1} \begin{pmatrix} I_{all}(\lambda 1) \\ \vdots \\ I_{all}(\lambda n) \end{pmatrix}$$

where a1 ($\lambda$1) to am ($\lambda$n) denote the coefficients for the fluorescent dyes at the standard density at the wavelengths $\lambda$1 to $\lambda$n, and $I_{all}(\lambda 1)$ to $I_{all}(\lambda n)$ denote the intensities of the fluorescence image at the wavelengths $\lambda$1 to $\lambda$n.

18 Claims, 8 Drawing Sheets

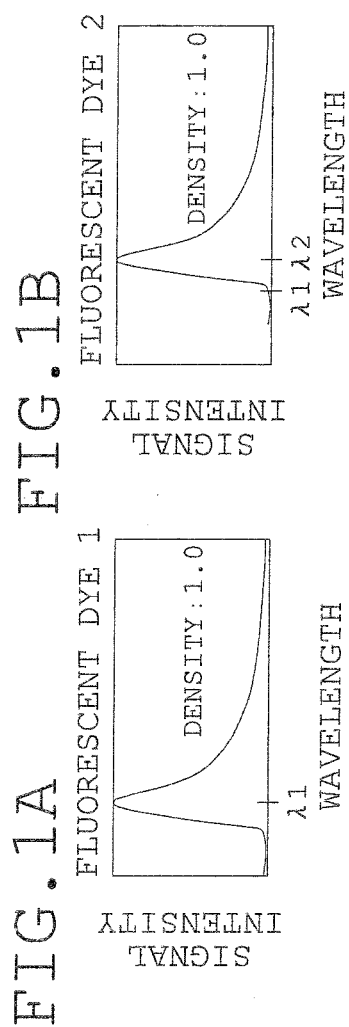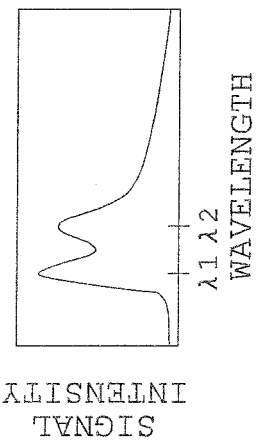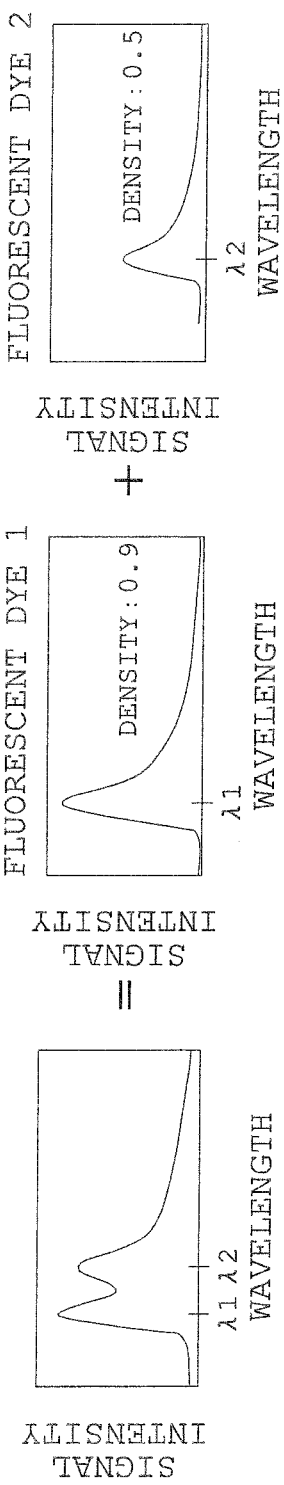

FLUORESCENCE OBSERVATION

EXCITATION LIGHT SPECTRUM

EXCITATION CUT FILTER

AUTO-FLUORESCENCE SPECTRUM AND THE SPECTRUM OF FLUORESCENT PROBE

A TRANSMITTABLE WAVELENGTH RANGE OF SPECTRAL OPTICAL ELEMENT

FLUORESCENCE ENDOSCOPE APPARATUS

This application claims benefits of Japanese Application No. 2010-059781 filed in Japan on Mar. 16, 2010, the contents of which are incorporated herein by reference.

BACKGROUND THE INVENTION

1. Field of the Invention

This invention relates to a florescence endoscope apparatus in which excitation light is radiated to a biological tissue and a lesion in the biological tissue is observed with fluorescent light that emits from the biological tissue.

2. Description of Related Art

In a fluorescence observation with an endoscope, if a living body is dyed with a plurality of fluorescent dyes or if auto-fluorescence of the living body occurs or contents such as stool emit fluorescence, the image of the living body is in a state in which many varieties of fluorescent lights are multiplexed. However, if the image of the living body in which the lights are multiplexed is observed as it is, it becomes hard to find the positions of lesions in which the fluorescent dyes accumulate, such as cancer. Accordingly, it is necessary to separate individual fluorescent lights.

Conventional methods for separating individual fluorescent lights from the multiplexed fluorescence image include a method which is aimed at calculating the densities of the respective fluorescent dyes in an object to be measured and is called Unmixing.

The procedure for separating fluorescent lights in Unmixing will be conceptually explained using FIG. 1. In this case, it is supposed that it is already known that two kinds of known fluorescent dyes (fluorescent substances) 1 and 2 exist in an object to be measured.

First, the fluorescence spectrum of each of the fluorescent dyes 1 and 2 which exist in the object to be measured is measured at a set standard density in advance. In this case, FIG. 1A shows one example of the fluorescence spectrum of the fluorescent dye 1 at the standard density, and FIG. 1B shows one example of the fluorescence spectrum of the fluorescent dye 2 at the standard density.

Next, the fluorescence spectrum of the measured object in which the fluorescent dyes 1 and 2 exist is measured. FIG. 1C shows one example of the fluorescence spectrum of the measured object.

Next, the densities of the fluorescent dyes 1 and 2 are calculated with the measurement data of the fluorescence spectra of the fluorescent dyes 1 and 2 at the standard density which are shown in FIGS. 1A and 1B, in order to obtain the measurement data of the fluorescence spectrum of the measured object which is shown in FIG. 1C. FIG. 1D schematically shows one example of the division of the measurement data of the fluorescence spectrum of the measured object shown in FIG. 1C into the respective fluorescence spectra of the fluorescent dyes 1 and 2 having predetermined densities.

Next, a method of calculating the densities of respective fluorescent dyes in Unmixing will be explained.

The signal intensity $I_{all}(\lambda n)$ of an object to be measured at a wavelength $\lambda n$ is the sum of the signal intensities of the respective fluorescent dyes at the wavelength $\lambda n$ and is expressed by the following equation (2):

$$I_{all}(\lambda n) = I1(\lambda n) + I2(\lambda n) + \ldots + Im(\lambda n) \quad (2).$$

where I1 denotes the signal intensity at the wavelength $\lambda n$ which is obtained from a fluorescent dye 1, I2 denotes the signal intensity at a wavelength $\lambda n$ which is obtained from a fluorescent dye 2, and Im denotes the signal intensity at a wavelength $\lambda n$ which is obtained from a fluorescent dye m.

Now, the signal intensity which is obtained from each of the fluorescent dyes is proportional to the density of each of the fluorescent dyes. Accordingly, in the case where m kinds of fluorescent dyes exist in the object to be measured, the signal intensities at a wavelength $\lambda n$ which are obtained from the respective fluorescent dyes can be expressed by the following equations (3a) to (3c):

$$I1(\lambda n) = a1(\lambda n) * D1 \quad (3a).$$

where D1 denotes the density of the fluorescent dye 1, and $a1(\lambda n)$ denotes the coefficient for the fluorescent dye 1 at the standard density at the wavelength $\lambda n$.

$$I2(\lambda n) = a2(\lambda n) * D2 \quad (3b).$$

where D2 denotes the density of the fluorescent dye 2, and $a2(\lambda n)$ denotes the coefficient for the fluorescent dye 2 at the standard density at the wavelength $\lambda n$.

$$Im(\lambda n) = am(\lambda n) * Dm \quad (3c).$$

where Dm denotes the density of the fluorescent dye m, and $am(\lambda n)$ denotes the coefficient for the fluorescent dye m at the standard density at the wavelength $\lambda n$.

In the case where it is supposed that m kinds of the fluorescent dyes exist in the object to be measured, the signal intensities of the measured object at n wavelength values $\lambda 1$ to $\lambda n$ can be expressed, for example, by the following matrix equation (4) with these equations (3a) to (3c):

$$\begin{pmatrix} I_{all}(\lambda 1) \\ I_{all}(\lambda 2) \\ \vdots \\ I_{all}(\lambda n) \end{pmatrix} = \begin{pmatrix} a1(\lambda 1) & a2(\lambda 1) & \ldots & am(\lambda 1) \\ a1(\lambda 2) & a2(\lambda 2) & \ldots & am(\lambda 2) \\ \vdots & \vdots & \vdots & \vdots \\ a1(\lambda n) & a2(\lambda n) & \ldots & am(\lambda n) \end{pmatrix} \begin{pmatrix} D1 \\ D2 \\ \vdots \\ Dn \end{pmatrix}. \quad (4)$$

In this case, in the left side of the matrix equation (4), $$\begin{pmatrix} I_{all}(\lambda 1) \\ I_{all}(\lambda 2) \\ \vdots \\ I_{all}(\lambda n) \end{pmatrix}$$

denotes the spectrum of the object to be measured.

Also, in the right side of the matrix equation (4), $$\begin{pmatrix} a1(\lambda 1) & a2(\lambda 1) & \ldots & am(\lambda 1) \\ a1(\lambda 2) & a2(\lambda 2) & \ldots & am(\lambda 2) \\ \vdots & \vdots & \vdots & \vdots \\ a1(\lambda n) & a2(\lambda n) & \ldots & am(\lambda n) \end{pmatrix}$$

denotes the fluorescent spectra of the respective fluorescent dyes at the standard density.

Accordingly, the densities of the respective fluorescent dyes D1, D2, . . . , and Dm are found by solving the following matrix equation (5):

$$\begin{pmatrix} D1 \\ D2 \\ \vdots \\ Dn \end{pmatrix} = \begin{pmatrix} a1(\lambda 1) & a2(\lambda 1) & \ldots & am(\lambda 1) \\ a1(\lambda 2) & a2(\lambda 2) & \ldots & am(\lambda 2) \\ \vdots & \vdots & \vdots & \vdots \\ a1(\lambda n) & a2(\lambda n) & \ldots & am(\lambda n) \end{pmatrix}^{-1} \begin{pmatrix} I_{all}(\lambda 1) \\ I_{all}(\lambda 2) \\ \vdots \\ I_{all}(\lambda n) \end{pmatrix}. \quad (5)$$

Besides, in the above-described matrix equation, when the number of varieties of the spectral images is equal to that of varieties of the fluorescent dyes (or, n=m), the equations are as many as varieties of the densities of the fluorescent dyes, so that the matrix equation can be uniquely solved. Also, when the number of varieties of the spectral images is larger than that of varieties of the fluorescent dyes (or, n>m), although the number of the equations is larger than that of varieties of the densities of the fluorescent dyes, the matrix equation can be solved with the least squares method or the like, in this case. As compared with this, when the number of varieties of the spectral images is smaller than that of varieties of the fluorescent dyes (or, n<m), the number of the equations is smaller than that of varieties of the densities of the fluorescent dyes, so that the matrix equation cannot be solved.

Accordingly, the method of Unmixing requires the premise that the number of varieties of the spectral images is equal to or larger than that of varieties of the fluorescent dyes (or, n≥m), As described above, according to the method of Unmixing, it is possible to calculate the density of each of the fluorescent dyes in each of pixels by acquiring the fluorescent spectra of the fluorescent dyes at the standard density in advance, acquiring a plurality of the spectral images, and performing the calculation of the matrix equation (5) in each of the pixels. The relation between n kinds of spectral images acquired in a set pixel and the spectrum in the matrix equation is conceptually shown in FIG. 2.

In FIG. 2, $I_{all}(\lambda 1)$ denotes the intensity of a spectral image 1 and $I_{all}(\lambda n)$ denotes the intensity of a spectral image n.

Conventionally, such a method of Unmixing is described, for example, in WO 2005/036143, Japanese Patent Kokai No. 2006-242899, or Japanese Patent Kokai No. 2005-181276.

SUMMARY OF THE INVENTION

A fluorescence endoscope apparatus according to the present invention, in which excitation light is radiated to a biological tissue and a lesion in the biological tissue is observed with fluorescent light that emits from the biological tissue, is characterized in that the fluorescence endoscope apparatus comprises: a fluorescence spectrum recording unit on which the respective fluorescence spectra of m kinds (where, 2≤m) of fluorescent dyes 1 to m that are presumed to be present in the biological tissue, at a standard density, are recorded; a fluorescence image acquiring unit by which a fluorescence image resulting from the biological tissue is acquired relative to each of n (where, m≤n) wavelength values λ1 to λn; and a fluorescent dye density-calculating unit by which the densities of the respective fluorescent dyes that are present in the biological tissue are calculated to be found in each of all the pixels in the fluorescence images, with the respective fluorescence spectra of the m kinds of the fluorescent dyes 1 to m at the standard density which are recorded on the fluorescence spectrum recording unit and the fluorescence images relative to the respective n wavelength values λ1 to λn which are acquired by the fluorescence image acquiring unit, wherein the fluorescent dye density-calculating unit calculates the densities D1 to Dm of the fluorescent dyes 1 to m in each of all the pixels in the fluorescence image and in all of the pixels with the following equation (1″), and, in the case where there exists a pixel in which at least one of the calculation values of the densities D1 to Dm of the fluorescent dyes 1 to m is smaller than 0, the fluorescent dye density-calculating unit substitutes a set value which is larger than the calculation value smaller than 0 for the density of fluorescent dye the calculation value of which is smaller than 0 in the equation (1″) and the densities of fluorescent dyes except fluorescent dye the calculation value of which is smaller than 0 are recalculated, relative to the pixel, when a1(λ1) to am(λn) denote the coefficients for the respective fluorescent dyes 1 to m at the standard density at the respective wavelengths λ1 to λn respectively, which are obtained from the fluorescence spectra of the respective fluorescent dyes 1 to m at the standard density that are recorded on the fluorescence spectrum recording unit, $I_{all}$(λ1) to $I_{all}$(λn) denote the intensities of the fluorescence image acquired by the fluorescence image acquiring unit at the wavelengths λ1 to λn, respectively, and D1 to Dm denote the densities of the respective fluorescent dyes 1 to m:

$$\begin{pmatrix} D1 \\ \vdots \\ Dm \end{pmatrix} = \begin{pmatrix} a1(\lambda 1) & \ldots & am(\lambda 1) \\ \vdots & \vdots & \vdots \\ a1(\lambda n) & \ldots & am(\lambda n) \end{pmatrix}^{-1} \begin{pmatrix} I_{all}(\lambda 1) \\ \vdots \\ I_{all}(\lambda n) \end{pmatrix}. \qquad \text{Equation (1″)}$$

Also, a fluorescence endoscope apparatus according to the present invention, in which excitation light is radiated to a biological tissue and a lesion in the biological tissue is observed with fluorescent light that emits from the biological tissue, is characterized in that the fluorescence endoscope apparatus comprises: a fluorescence spectrum recording unit on which the respective fluorescence spectra of two kinds of fluorescent dyes 1 and 2 that are presumed to be present in the biological tissue, at the standard density, are recorded; a fluorescence image acquiring unit by which a fluorescence image resulting from the biological tissue is acquired relative to each of two wavelength values λ1 and λ2; and a fluorescent dye density-calculating unit by which the densities of the respective fluorescent dyes that are present in the biological tissue are calculated to be found in each of all the pixels in the fluorescence images, with the respective fluorescence spectra of the two kinds of the fluorescent dyes 1 and 2 at the standard density which are recorded on the fluorescence spectrum recording unit and the fluorescence images relative to the respective two wavelength values λ1 and λ2 which are acquired by the fluorescence image acquiring unit, wherein the fluorescent dye density-calculating unit calculates the densities D1 and D2 of the fluorescent dyes 1 and 2 in each of all the pixels in the fluorescence image and in all of the pixels with the following equation (1), and, in the case where there exists a pixel in which one of the calculation values of the densities D1 and D2 of the fluorescent dyes 1 and 2 is smaller than 0, the fluorescent dye density-calculating unit substitutes a set value which is larger than the calculation value smaller than 0 for the density of fluorescent dye the calculation value of which is smaller than 0 in the equation (1) and the density of the other fluorescent dye is recalculated, relative to the pixel, when a1(λ1) denotes the coefficient for the fluorescent dye 1 at the standard density at the wavelength λ1, which is obtained from the fluorescence spectra of the respective fluorescent dyes 1 and 2 at the standard density that are recorded on the fluorescence spectrum recording unit, a1(λ2) denotes the coefficient for the fluorescent dye 1 at the standard density at the wavelength λ2, which is obtained from the fluorescence spectra of the respective fluorescent dyes 1 and 2 at the standard density that are recorded on the fluorescence spectrum recording unit, a2(λ1) denotes the coefficient for the fluorescent dye 2 at the standard density at the wavelength λ1, which is obtained from the fluorescence spectra of the respective fluorescent dyes 1 and 2 at the standard density that are recorded on the fluorescence spectrum recording unit, a2(λ2) denotes the coefficient for the fluorescent dye 2 at the standard density at the wavelength λ2, which is obtained from the fluorescence spectra of the respective fluorescent dyes 1 and 2 at the standard density that are recorded on the fluorescence spectrum recording unit, $I_{all}(\lambda 1)$ denotes the intensity of the fluorescence image acquired by the fluorescence image acquiring unit at the wavelength $\lambda 1$, $I_{all}(\lambda 2)$ denotes the intensity of the fluorescence image acquired by the fluorescence image acquiring unit at the wavelength $\lambda 2$, D1 denotes the density of the fluorescent dye 1, and D2 denotes the density of the fluorescent dye 2:

$$\begin{pmatrix} D1 \\ D2 \end{pmatrix} = \begin{pmatrix} a1(\lambda 1) & a2(\lambda 1) \\ a1(\lambda 2) & a2(\lambda 2) \end{pmatrix}^{-1} \begin{pmatrix} I_{all}(\lambda 1) \\ I_{all}(\lambda 2) \end{pmatrix}. \qquad \text{Equation (1)}$$

Also, a fluorescence endoscope apparatus according to the present invention, in which excitation light is radiated to a biological tissue and a lesion in the biological tissue is observed with fluorescent light that emits from the biological tissue, is characterized in that the fluorescence endoscope apparatus comprises: a fluorescence spectrum recording unit on which the respective fluorescence spectra of three kinds of fluorescent dyes 1 to 3 that are presumed to be present in the biological tissue, at the standard density, are recorded; a fluorescence image acquiring unit by which a fluorescence image resulting from the biological tissue is acquired relative to each of three wavelength values $\lambda 1$ to $\lambda 3$; and a fluorescent dye density-calculating unit by which the densities of the respective fluorescent dyes that are present in the biological tissue are calculated to be found in each of all the pixels in the fluorescence images, with the respective fluorescence spectra of the three kinds of the fluorescent dyes 1 to 3 at the standard density which are recorded on the fluorescence spectrum recording unit and the fluorescence images relative to the respective three wavelength values $\lambda 1$ to $\lambda 3$ which are acquired by the fluorescence image acquiring unit, wherein the fluorescent dye density-calculating unit calculates the densities D1 to D3 of the fluorescent dyes 1 to 3 in each of all the pixels in the fluorescence image and in all of the pixels with the following equation (1'), and, in the case where there exists a pixel in which at least one of the calculation values of the densities D1 to D3 of the fluorescent dyes 1 to 3 is smaller than 0, the fluorescent dye density-calculating unit substitutes a set value which is larger than the calculation value smaller than 0 for the density of fluorescent dye the calculation value of which is smaller than 0 in the equation (1') and the densities of fluorescent dyes except fluorescent dye the calculation value of which is smaller than 0 are recalculated, relative to the pixel, when $a1(\lambda 1)$ denotes the coefficient for the fluorescent dye 1 at the standard density at the wavelength $\lambda 1$, which is obtained from the fluorescence spectra of the respective fluorescent dyes 1 to 3 at the standard density that are recorded on the fluorescence spectrum recording unit, $a1(\lambda 2)$ denotes the coefficient for the fluorescent dye 1 at the standard density at the wavelength $\lambda 2$, which is obtained from the fluorescence spectra of the respective fluorescent dyes 1 to 3 at the standard density that are recorded on the fluorescence spectrum recording unit, $a1(\lambda 3)$ denotes the coefficient for the fluorescent dye 1 at the standard density at the wavelength $\lambda 3$, which is obtained from the fluorescence spectra of the respective fluorescent dyes 1 to 3 at the standard density that are recorded on the fluorescence spectrum recording unit, $a2(\lambda 1)$ denotes the coefficient for the fluorescent dye 2 at the standard density at the wavelength $\lambda 1$, which is obtained from the fluorescence spectra of the respective fluorescent dyes 1 to 3 at the standard density that are recorded on the fluorescence spectrum recording unit, $a2(\lambda 2)$ denotes the coefficient for the fluorescent dye 2 at the standard density at the wavelength $\lambda 2$, which is obtained from the fluorescence spectra of the respective fluorescent dyes 1 to 3 at the standard density that are recorded on the fluorescence spectrum recording unit, $a2(\lambda 3)$-denotes the coefficient for the fluorescent dye 2 at the standard density at the wavelength $\lambda 3$, which is obtained from the fluorescence spectra of the respective fluorescent dyes 1 to 3 at the standard density that are recorded on the fluorescence spectrum recording unit, $a3(\lambda 1)$ denotes the coefficient for the fluorescent dye 3 at the standard density at the wavelength $\lambda 1$, which is obtained from the fluorescence spectra of the respective fluorescent dyes 1 to 3 at the standard density that are recorded on the fluorescence spectrum recording unit, $a3(\lambda 2)$ denotes the coefficient for the fluorescent dye 3 at the standard density at the wavelength $\lambda 2$, which is obtained from the fluorescence spectra of the respective fluorescent dyes 1 to 3 at the standard density that are recorded on the fluorescence spectrum recording unit, $a3(\lambda 3)$ denotes the coefficient for the fluorescent dye 3 at the standard density at the wavelength $\lambda 3$, which is obtained from the fluorescence spectra of the respective fluorescent dyes 1 to 3 at the standard density that are recorded on the fluorescence spectrum recording unit, $I_{all}(\lambda 1)$ denotes the intensity of the fluorescence image acquired by the fluorescence image acquiring unit at the wavelength $\lambda 1$, $I_{all}(\lambda 2)$ denotes the intensity of the fluorescence image acquired by the fluorescence image acquiring unit at the wavelength $\lambda 2$, $I_{all}(\lambda 3)$ denotes the intensity of the fluorescence image acquired by the fluorescence image acquiring unit at the wavelength $\lambda 3$, D1 denotes the density of the fluorescent dye 1, D2 denotes the density of the fluorescent dye 2, and D3 denotes the density of the fluorescent dye 3:

$$\begin{pmatrix} D1 \\ D2 \\ D3 \end{pmatrix} = \begin{pmatrix} a1(\lambda 1) & a2(\lambda 1) & a3(\lambda 1) \\ a1(\lambda 2) & a2(\lambda 2) & a3(\lambda 2) \\ a1(\lambda 3) & a2(\lambda 3) & a3(\lambda 3) \end{pmatrix}^{-1} \begin{pmatrix} I_{all}(\lambda 1) \\ I_{all}(\lambda 2) \\ I_{all}(\lambda 3) \end{pmatrix}. \qquad \text{Equation (1')}$$

These and other features and advantages of the present invention will becomes apparent from the following detailed description of the preferred embodiments when taken in conjunction with the accompanying drawings.

BRIEF DESCRIPTION OF THE DRAWINGS

FIG. 1 is an explanatory view conceptually showing a procedure for the separation into two kinds of fluorescent lights through Unmixing FIG. 1A is a graph showing one example of the fluorescence spectrum of a fluorescent dye 1 at the standard density, FIG. 1B is a graph showing one example of the fluorescence spectrum of a fluorescent dye 2 at the standard density, FIG. 1C is a graph showing one example of the fluorescence spectrum of an object to be measured which is measured, and FIG. 1D is a graph schematically showing one example of the division of the measurement data of the fluorescence spectrum of the measured object shown in FIG. 1C into the fluorescence spectra of the respective fluorescent dyes 1 and 2 with set densities.

FIG. 5 is a graph showing one example of optical characteristics in a fluorescence observation with the fluorescence endoscope apparatus shown in FIG. 4.

DETAILED DESCRIPTION OF THE PREFERRED EMBODIMENTS

Figure 2:
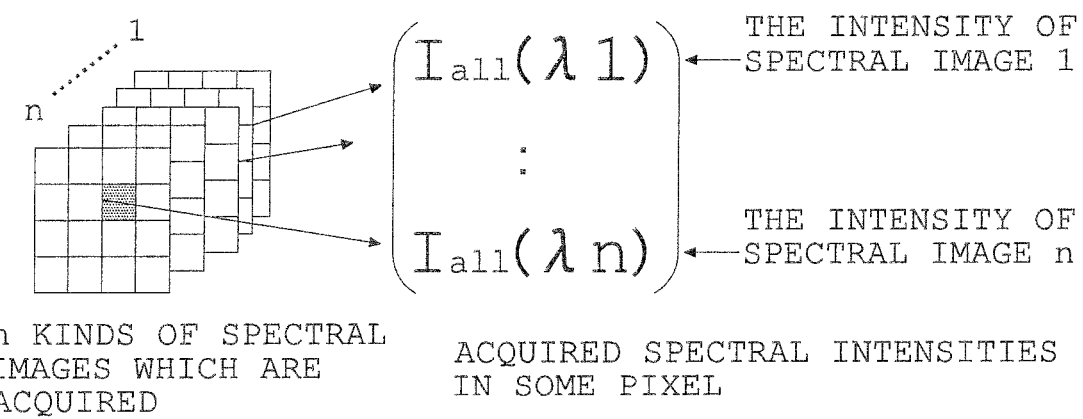
FIG. 2 is an explanatory view conceptually showing the relation between n kinds of spectral images which are acquired in a set pixel and spectra in the matrix equation.
Figure 3:
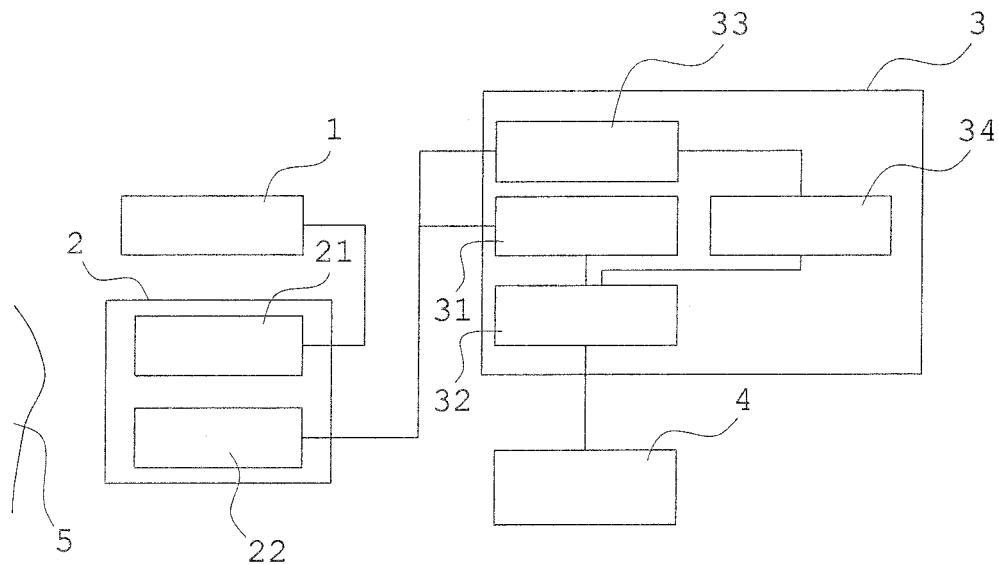
FIG. 3 is a block diagram schematically showing a constitution of the whole of a fluorescence endoscope apparatus which is common to the embodiments of the present invention.

FIG. 3 is a block diagram schematically showing a constitution of the whole of a fluorescence endoscope apparatus which is common to the embodiments of the present invention.

The fluorescence endoscope apparatus which is shown in FIG. 3 includes a light source unit 1, an endoscope top end insertion unit 2, an image processing unit 3, and a display unit 4.

The light source unit 1 includes a light source and an excitation filter and is formed in such a way that the light source unit 1 can emit light in a range of wavelengths for excitation.

The endoscope top end insertion unit 2 includes an illumination optical system 21 and an image-pick up optical system 22.

The illumination optical system 21 is formed in such a way that the illumination optical system 21 radiates excitation light from the light source unit 1 to a biological tissue 5.

The image-pick up optical system 22 includes an objective optical system, an image-forming optical system, an excitation cut filter, a spectral optical element, an image sensor, and so on (which are omitted in the drawings), the image-pick up optical system 22 has a function as a fluorescence image acquiring unit for the present invention, through control by a set control means which is omitted in the drawings, and the image-pick up optical unit 22 is formed in such a way that a fluorescence image resulting from the biological tissue 5 can be acquired relative to each of n (where, n≤2) wavelength values λ1 to λn by the image-pick up optical system 22.

The image processing unit 3 includes a frame memory 31, an image processing device 32, a fluorescence spectrum recording unit 33, and a fluorescent dye density-calculating unit 34.

Respective image signals which are acquired through the image-pick up optical system 22 are written onto the frame memory 31.

The respective image signals which are written on the frame memory 31 are synthesized by the image processing device 32. In this case, in order to make it possible to easily distinguish a normal tissue region and a lesion tissue region, the image processing devise 32 assigns the image signals color phases which vary with fluorescent dye, respectively, and the image-processing device 32 transforms the image signals into the output signals of the intensities on the basis of the densities of the fluorescent dyes which are calculated by the fluorescent dye density-calculating unit 34.

The image which is processed through the image-processing devise 32 is displayed by the display unit 4.

The respective fluorescence spectra of m kinds (where 2≤m≤n) of fluorescent dyes 1 to m which are presumed to be present in the biological tissue 5, at the standard density, are recorded on the fluorescence spectrum recording unit 33.

When a1(λ1) to am(λn) denote the coefficients for the fluorescent dyes 1 to m at the standard density at the respective wavelengths λ1 to λn respectively, which are obtained from the respective fluorescence spectra of the fluorescent dyes 1 to m at the standard density that are recorded on the fluorescence spectrum recording unit 33, $I_{all}(\lambda 1)$ to $I_{all}(\lambda n)$ denote the intensities of the fluorescence image acquired by the fluorescence image acquiring unit at the respective wavelengths λ1 to λn, respectively, and D1 to Dm denote the respective densities of the fluorescent dyes 1 to m, the fluorescent dye density-calculating unit 34 calculates the densities D1 to Dm of the fluorescent dyes 1 to m with the equation (1″). In this case, in the case where there exists a pixel in which at least one of the calculation values of the densities D1 to Dm of the fluorescent dyes 1 to m is smaller than 0, the fluorescent dye density-calculating unit 34 substitutes a set value which is larger than the value of the calculated density smaller than 0 for the density of a fluorescent dye the calculation value of which is smaller than 0 in the equation (1″) and the densities of fluorescent dyes except the fluorescent dye the calculation value of which is smaller than 0 are recalculated, relative to the pixel:

$$\begin{pmatrix} D1 \\ \vdots \\ Dm \end{pmatrix} = \begin{pmatrix} a1(\lambda 1) & \cdots & am(\lambda 1) \\ \vdots & \vdots & \vdots \\ a1(\lambda n) & \cdots & am(\lambda n) \end{pmatrix}^{-1} \begin{pmatrix} I_{all}(\lambda 1) \\ \vdots \\ I_{all}(\lambda n) \end{pmatrix}. \quad \text{Equation (1″)}$$

That is to say, the fluorescence endoscope apparatus which is shown in FIG. 3 is formed in such a way that, when the calculation value of the density of some fluorescent dye is largely different from presumed values to become a minus value, the fluorescent dye density-calculating unit 34 substitutes for the minus calculation value a value within the presumed range which is larger than the minus calculation value (for example, 0), and the fluorescent dye density-calculating unit 34 recalculates the densities of fluorescent dyes except fluorescent dye the calculation value of which is smaller than 0.

For example, in a constitution for obtaining fluorescence images for two kinds of fluorescent dyes 1 and 2 at two wavelength values λ1 and λ2, the matrix equation for finding the density D1 of the fluorescent dye 1 and the density D2 of the fluorescent dye 2 is expressed by the following equation (1):

$$\begin{pmatrix} D1 \\ D2 \end{pmatrix} = \begin{pmatrix} a1(\lambda 1) & a2(\lambda 1) \\ a1(\lambda 2) & a2(\lambda 2) \end{pmatrix}^{-1} \begin{pmatrix} I_{all}(\lambda 1) \\ I_{all}(\lambda 2) \end{pmatrix}. \qquad \text{Equation (1)}$$

In this case, as a result of the calculation of the matrix equation (1) by the fluorescent dye density-calculating unit 34, the density D2 of the fluorescent dye 2 may has a minus value for example.

However, in fact, the minimum of the density of fluorescent dye is 0 and the density of fluorescent dye cannot have a minus value. And, in the case where the density D2 of the fluorescent dye 2 is calculated to have a minus calculation value, there is a high probability that the density D1 of the fluorescent dye 1 may be calculated to be larger than the actual density of the fluorescent dye 1.

In this respect, a detailed explanation will be performed using equation.

For example, in the constitution for obtaining fluorescent images for the above-described two kinds of the fluorescent dyes 1 and 2 at the two wavelength values λ1 and λ2, the signal intensity $I_{all}(\lambda 1)$ of an object to be measured at the wavelength λ1 is expressed by the sum of the signal intensities of the two kinds of the fluorescent dyes 1 and 2 at the wavelength λ1 and can be expressed by the following equation (2'):

$$I_{all}(\lambda 1) = a1(\lambda 1)*D1 + a2(\lambda 1)*D2 \qquad (2').$$

where a1(λ1) denotes the coefficient for the fluorescent dye 1 at the standard density at the wavelength λ1, and a2(λ1) denotes the coefficient for the fluorescent dye 2 at the standard density at the wavelength λ1.

In this case, the minimum values of the densities D1 and D2 of the fluorescent dyes 1 and 2 are 0, respectively, and cannot have a minus value. Accordingly, the minimum value of the brightness (signal intensity) of the fluorescent dye 1 at the wavelength λ1 is 0, and the minimum value of the brightness (signal intensity) of the fluorescent dye 2 at the wavelength λ1 is 0.

As a result, in the above equation (2'), when the brightness (signal intensity) a1(λ1)*D1 of the fluorescent dye 1 at the wavelength λ1 is 0 for example, the brightness (signal intensity) a2(λ1)*D2 of the fluorescent dye 2 at the wavelength λ1 theoretically becomes equal to the brightness (signal intensity) $I_{all}(\lambda 1)$ of the object to be measured at the wavelength λ1. Also, when the brightness (signal intensity) a2(λ1)*D2 of the fluorescent dye 2 at the wavelength λ1 is 0 for example, the brightness (signal intensity) a1(λ1)*D1 of the fluorescent dye 1 at the wavelength λ1 theoretically becomes equal to the brightness (signal intensity) $I_{all}(\lambda 1)$ of the object to be measured at the wavelength λ1.

Accordingly, in the above matrix equation (1), when the density D2 of the fluorescent dye 2 at the wavelength λ1 is calculated to have a minus calculation value for example, the brightness (signal intensity) a2(λ1)*D2 of the fluorescent dye 2 at the wavelength λ1 is calculated to have a minus calculation value. As a result, in the above equation (2'), the calculation value of the brightness (signal intensity) a1(λ1)*D1 of the fluorescent dye 1 at the wavelength λ1 becomes a brighter value than the brightness (signal intensity) $I_{all}(\lambda 1)$ of the object to be measured at the wavelength λ1, so that the calculation value of the brightness (signal intensity) a1(λ1)*D1 of the fluorescent dye 1 at the wavelength λ1 exceeds the theoretical maximum value of the brightness (signal intensity) a1(λ1)*D1 of the fluorescent dye 1 at the wavelength λ1.

When an image which is reconstructed on the basis of such a calculation value relative to the fluorescent dye 1 is displayed by the display unit 4, the signal intensity in the region on which the fluorescent dyes 1 accumulate becomes too strong, so that noise easily occurs.

As in the fluorescence endoscope shown in FIG. 3, the fluorescent dye density-calculating unit 34 substitutes a value within the presumed range (for example, 0) for the density D2 of the fluorescent dye 2 in the matrix equation (1), and the fluorescent dye density-calculating unit 34 recalculates the density D1 of the fluorescent dye 1, so that it is possible to make a small difference between the calculation value of the density D1 of the fluorescent dye 1 and the actual density. As a result, in the case where an image which is reconstructed relative to the fluorescent dye 1 is displayed by the display unit 4, it is possible to prevent noise from occurring in the region on which the fluorescent dyes 1 accumulate, so that the image becomes easy to observe.

Specific examples of the recalculation process of the densities of fluorescent dyes by the fluorescent dye density-calculating unit 34 in the fluorescence endoscope apparatus having the constitution shown in FIG. 3 will be explained as embodiments of the present invention, below.

First Embodiment

An Example of the Substitution of 0

The fluorescence endoscope apparatus of the first embodiment is formed in such a way that, in the case of obtaining fluorescence images for three kinds of fluorescent dyes 1 to 3 at three wavelength values λ1 to λ3, when there exists a pixel in which at least one of the calculation values of the densities D1 to D3 of the fluorescent dyes 1 to 3 which are calculated with the matrix equation (1') for finding the densities D1 to D3 of the fluorescent dyes 1 to 3 is smaller than 0, the fluorescent dye density-calculating unit 34 substitutes 0 for the density of fluorescent dye the calculation value of which is smaller than 0, in the equation (1'), and the fluorescent dye density-calculating unit 34 recalculates the densities of fluorescent dyes except fluorescent dye the calculation value of which is smaller than 0, relative to the pixel.

In the case where there exists a pixel in which the calculation value of the density D3 of the fluorescent dye 3 becomes smaller than 0 for example, the fluorescent dye density-calculating unit 34 substitutes 0 for the density D3 of the fluorescent dye 3 in the equation (1') to perform a recalculation, or to calculate the following equation (1' α) to find the densities D1 and D2 of the fluorescent dyes 1 and 2, relative to the pixel $$\begin{pmatrix} a_{11} & a_{12} & a_{13} \\ a_{21} & a_{22} & a_{23} \\ a_{31} & a_{32} & a_{33} \end{pmatrix} \begin{pmatrix} D_1 \\ D_2 \\ 0 \end{pmatrix} = \begin{pmatrix} I_g \\ I_b \\ I_r \end{pmatrix} \Rightarrow \begin{pmatrix} a_{11} & a_{12} \\ a_{21} & a_{22} \\ a_{31} & a_{32} \end{pmatrix} \begin{pmatrix} D_1 \\ D_2 \end{pmatrix} = \begin{pmatrix} I_g \\ I_b \\ I_r \end{pmatrix}. \qquad (1'\alpha)$$

Besides, $a_{11}$ to $a_{33}$ are simply shown in the equation (1' α) as the coefficients a1(λ1) to a3(λ3) for the respective fluorescent dyes 1 to 3 at the standard density at the respective wavelengths λ1 to λ3, for the sake of convenience. Also, Ig to Ir are simply shown in the equation (1' α) as the intensities $I_{all}(λ1)$ to $I_{all}(λ3)$ of the fluorescence image acquired by the fluorescence image acquiring unit (the image-pick up optical system 22 and a spectral optical element-controlling unit 22f) at the respective wavelengths λ1 to λ3, for the sake of convenience.

Also, in the case where there exists a pixel in which the calculation values of the densities D2 and D3 of the fluorescent dyes 2 and 3 become smaller than 0, for example, the fluorescent dye density-calculating unit 34 substitutes 0 for the densities D2 and D3 of the fluorescent dyes 2 and 3 in the equation (1') respectively to perform a recalculation, or to calculate the following equation (1' β) to find the density D1 of the fluorescent dye 1, relative to the pixel.

$$\begin{pmatrix} a_{11} & a_{12} & a_{13} \\ a_{21} & a_{22} & a_{23} \\ a_{31} & a_{32} & a_{33} \end{pmatrix} \begin{pmatrix} D_1 \\ 0 \\ 0 \end{pmatrix} = \begin{pmatrix} I_g \\ I_b \\ I_r \end{pmatrix} \Rightarrow \begin{pmatrix} a_{11} \\ a_{21} \\ a_{31} \end{pmatrix} (D_1) = \begin{pmatrix} I_g \\ I_b \\ I_r \end{pmatrix}. \quad (1'β)$$

Besides, although the number of the equations (three) is larger than that of varieties of the densities (one kind) in the matrix equation (1' β), it is possible to solve the matrix equation (1' β) with the least squares method or the like, in this case.

As in the fluorescence endoscope apparatus of the first embodiment, when the fluorescent dye density-calculating unit 34 substitutes 0 for the density D3 of the fluorescent dye 3 (or the density D2 of the fluorescent dye and the density D3 of the fluorescent dye 3) the calculation value of which is smaller than 0 to recalculate the densities D1 and D2 of the fluorescent dyes 1 and 2 except the fluorescent dye 3 the calculation value of which is smaller than 0 (or the density D1 of the fluorescent dye 1), errors in the densities D1 and D2 of the fluorescent dyes 1 and 2 except the fluorescent dye 3 the calculation value of which is smaller than 0 (or the density D1 of the fluorescent dye D1) can be made to become small. As a result, when the image of the fluorescent dye 1 (or the images of the fluorescent dyes 1 and 2) is displayed on the display device, light spots do not occur in the region (regions) on which the fluorescent dyes 1 (or the fluorescent dyes 1 and 2) accumulate, and the image becomes easy to observe.

In addition, the number of columns in the matrix equation can be decreased.

Second Embodiment

An Example of the Substitution of a Number Different from 0

The fluorescence endoscope apparatus of the second embodiment is formed in such a way that, in the case of obtaining fluorescence images for three kinds of fluorescent dyes 1 to 3 at three wavelength values λ1 to λ3, when there exists a pixel in which at least one of the calculation values of the densities D1 to D3 of the fluorescent dyes 1 to 3 which are calculated with the matrix equation (1') for finding the densities D1 to D3 of the fluorescent dyes 1 to 3 is smaller than 0, the fluorescent dye density-calculating unit 34 substitutes a number different from 0 for the density of a fluorescent dye the calculation value of which is smaller than 0, in the equation (1'), and the fluorescent dye density-calculating unit 34 recalculates the densities of fluorescent dyes except fluorescent dye the calculation value of which is smaller than 0, relative to the pixel.

Values which the fluorescent dye density-calculating unit 34 substitutes for the density of fluorescent dye the calculation value of which is smaller than 0 for the sake of recalculation are not limited to 0 as in the fluorescence endoscope apparatus of the first embodiment, and it is possible to reduce noise even though a value which approximates to 0 is substituted for the density of fluorescent dye the calculation value of which is smaller than 0 to recalculate the densities of fluorescent dyes except fluorescent dye the calculation value of which is smaller than 0. In this case, it is preferred that a value which approximates to 0 to the utmost is substituted for the density of fluorescent dye the calculation value of which is smaller than 0. In recalculation, the more a value which is substituted for the density of fluorescent dye the calculation value of which is smaller than 0 approximates to 0, the smaller it is possible to make errors in the recalculation values of the densities of fluorescent dyes except fluorescent dye the calculation value of which is smaller than 0.

In the case where there exists a pixel in which at least one of the calculation values of the densities D1 to D3 of the fluorescent dyes 1 to 3 is smaller than 0 for example, the fluorescence endoscope apparatus of the present embodiment may be formed in such a way that the fluorescent dye density-calculating unit 34 substitutes for the density of fluorescent dye the calculation value of which is smaller than 0 a set value the absolute value of which is smaller than that of the calculation value smaller than 0, in the equation (1') to recalculate the densities of fluorescent dyes except fluorescent dye the calculation value of which is smaller than 0, relative to the pixel.

In addition, in the case where there exists a pixel in which at least one of the calculation values of the densities D1 to D3 of the fluorescent dyes 1 to 3 is smaller than 0 for example, it is more preferred that the fluorescence endoscope apparatus of the present embodiment is formed in such a way that the fluorescent dye density-calculating unit 34 substitutes for the density of fluorescent dye the calculation value of which is smaller than 0 a set value the absolute value of which is one half or less of the absolute value of the calculation value smaller than 0, in the equation (1') to recalculate the densities of fluorescent dyes except fluorescent dye the calculation value of which is smaller than 0, relative to the pixel.

Third Embodiment

An Example of the Substitution of the Calculation Value of the Density of a Fluorescent Dye in a Set Pixel that is Located in the Vicinity of a Pixel in which the Fluorescent Dye has a Calculation Value Smaller than 0

The fluorescence endoscope apparatus of the third embodiment is formed in such a way that, in the case of obtaining fluorescence images for three kinds of fluorescent dyes 1 to 3 at three wavelength values λ1 to λ3, when there exists a pixel in which at least one of the densities D1 to D3 of the fluorescent dyes 1 to 3 which are calculated with the matrix equation (1') for finding the densities D1 to D3 of the fluorescent dyes 1 to 3 is smaller than 0, the fluorescent dye density-calculating unit 34 substitutes for the density of fluorescent dye the calculation value of which is smaller than 0 the calculation value of density which the corresponding fluorescent dye the calculation value of which is smaller than 0 in the pixel has in a set pixel that is located in the vicinity of the pixel and which is larger than the calculation value that is smaller than 0, in the equation (1'), and the fluorescent dye density-calculating unit 34 recalculates the densities of fluorescent dyes except fluorescent dye the calculation value of which is smaller than 0, relative to the pixel.

For example, relative to a pixel in which there exists a fluorescent dye the calculation value of density of which is smaller than 0, the fluorescence endoscope apparatus of the present embodiment is formed in such a way that the fluorescent dye density-calculating unit 34 substitutes for the density of fluorescent dye the calculation value of which is smaller than 0 the calculation value of density which the corresponding fluorescent dye has in a pixel adjacent to the pixel and which is larger than the calculation value that is smaller than 0, to perform recalculation. Or, the fluorescence endoscope apparatus of the present embodiment is formed in such a way that the fluorescent dye density-calculating unit 34 substitutes for the density of the fluorescent dye the calculation value of which is smaller than 0 the average of the calculation values of density which the corresponding fluorescent dye has in pixels surrounding the pixel and which are larger than the calculation value that is smaller than 0, to perform recalculation. In this case, the range of pixels surrounding the pixel is not limited to the range of the pixels adjacent to the pixel and may include the range of pixels which are a few pixels away from the pixels adjacent to the pixel.

Besides, it is preferred that a positive number is used as the calculation value of density which the fluorescent dye density-calculating unit 34 substitutes relative to a pixel in which there exists a fluorescent dye the calculation value of density of which is smaller than 0 and which the corresponding fluorescent dye has in a set pixel that is located in the vicinity of the pixel Fourth Embodiment A Process for Shortening Calculation Time The fluorescence endoscope apparatus of the fourth embodiment is formed in such a way that, in the case where the densities of fluorescent dyes except fluorescent dye the calculation value of which is smaller than 0 are recalculated, in the equation (1"), in the coefficients a1(λ1) to am(λn) for the respective fluorescent dyes 1 to m at the standard density at the respective wavelengths λ1 to λn and the intensities $I_{all}(\lambda 1)$ to $I_{all}(\lambda n)$ of the fluorescence image acquired by the fluorescence image acquiring unit at the respective wavelengths λ1 to λn, coefficients and fluorescence intensities at the standard density at wavelengths except a wavelength component at which the fluorescence intensity of fluorescent dye the density of which is targeted at the recalculation is large are excluded from an object for the recalculation, the number of varieties of the wavelengths is made to become equal to that of varieties of the fluorescent dyes, and the recalculation is performed.

A matrix equation in which the number of varieties of wavelengths (the number of equations) is larger than the number of varieties of fluorescent dyes (varieties of densities of fluorescent dyes) can be solved with the least squares method, for example. However, it takes too a lot of time to perform calculation with the least squares method, so that it may be hard to display a moving image on the basis of the densities which are obtained by the calculation.

In such a case, the number of the equations is decreased to become equal to the number of varieties of the densities of fluorescent dyes and then recalculation is performed, so that it is possible to shorten calculation time and it becomes easy to display a moving image.

In the case where the calculation value of the density D3 of the fluorescent dye 3 becomes smaller than 0 for example, the fluorescent dye density-calculating unit 34 substitutes 0 for the density D3 of the fluorescent dye 3 in the equation (1'), so that the equation (1') changes into the equation (1' α). In addition, the fluorescent dye density-calculating unit 34 decreases the number of row components of the matrix equation in the fluorescence endoscope apparatus of the fourth embodiment, like the following equation (1' α'), so that the number of the equations is made to become equal to the number of varieties of the densities of fluorescent dyes.

$$\begin{pmatrix} a_{11} & a_{12} \\ a_{21} & a_{22} \\ a_{31} & a_{32} \end{pmatrix} \begin{pmatrix} D_1 \\ D_2 \end{pmatrix} = \begin{pmatrix} I_g \\ I_b \\ I_r \end{pmatrix}. \tag{1'α}$$

$$\begin{pmatrix} a_{11} & a_{12} \\ a_{21} & a_{22} \end{pmatrix} \begin{pmatrix} D_1 \\ D_2 \end{pmatrix} = \begin{pmatrix} I_g \\ I_b \end{pmatrix}. \tag{1'α'}$$

Besides, in this case, a wavelength component which largely contributes to the densities D1 and D2 of the fluorescent dyes 1 and 2 that are recalculated (for example, a wavelength component at which the fluorescence intensities of the fluorescent dyes 1 and 2 are large) is kept in order to minimize error to the utmost. In this explanation, the fluorescence intensities of the fluorescent dyes 1 and 2 at the wavelength components Ig and Ib are considered to be larger than those at the wavelength component Ir.

Next, examples of a fluorescence endoscope apparatus of the present invention will be explained.

Figure 4:
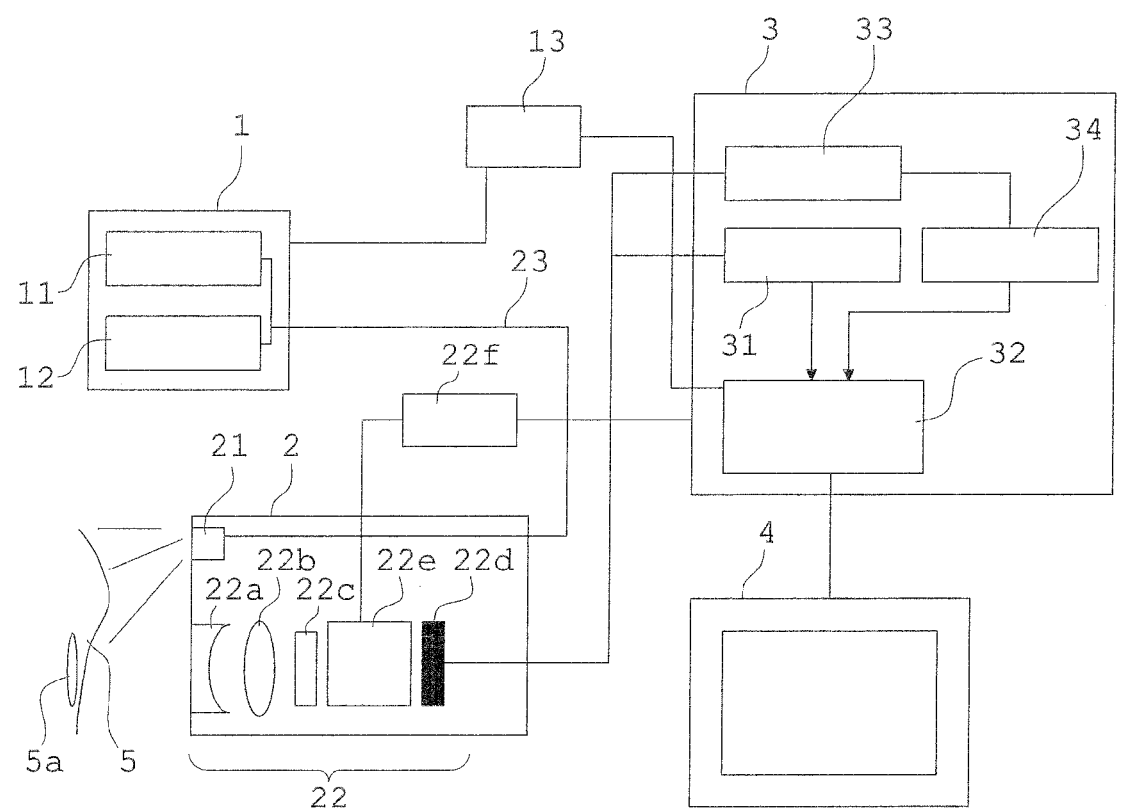
FIG. 4 is a block diagram showing a constitution of the whole of a fluorescence endoscope apparatus which is common to the examples of the present invention.
Figure 5A:
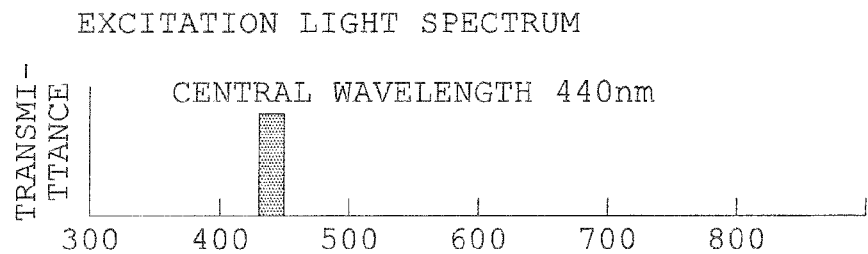
FIG. 5A is a view showing the spectrum of excitation light.
Figure 5B:
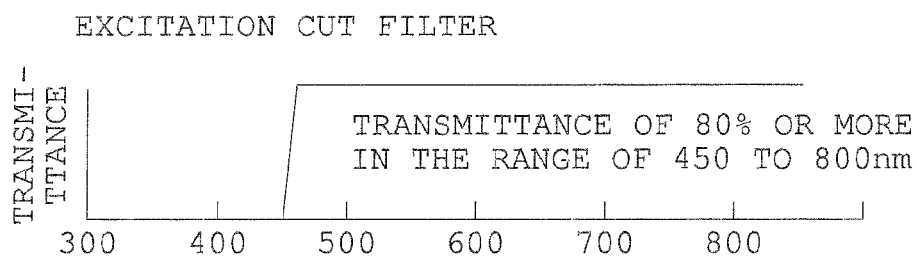
FIG. 5B is a view showing the spectral transmittance of an excitation light cut filter.
Figure 5C:
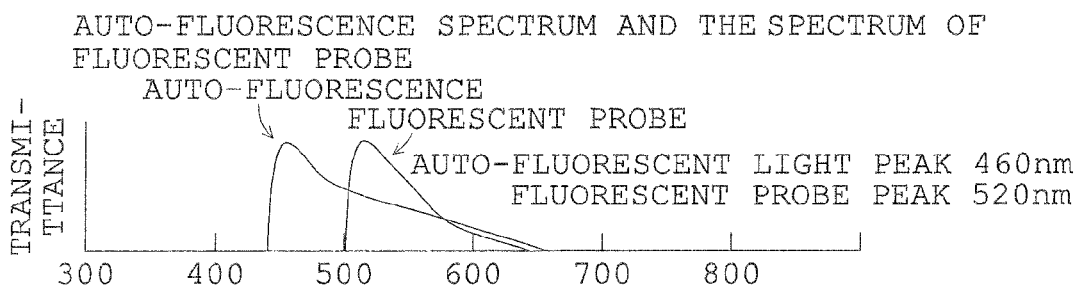
FIG. 5C is a view showing an auto-fluorescence spectrum and the fluorescence spectrum of a fluorescent dye.
Figure 5D:
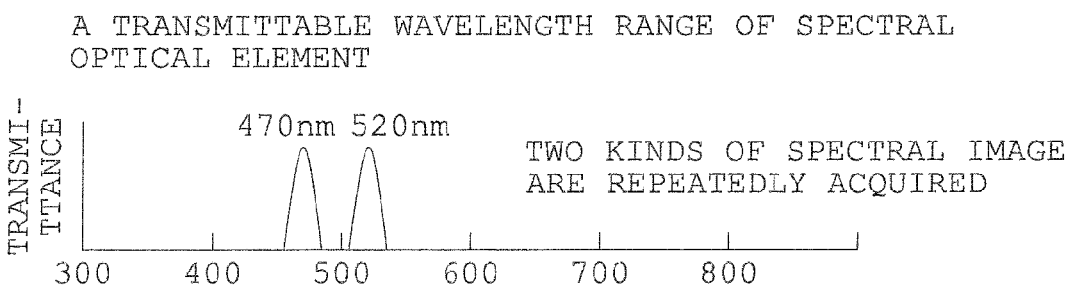
FIG. 5D is a view showing a range within which a spectral optical element that is used for the fluorescence endoscope apparatus shown in FIG. 4 repeatedly changes transmittable wavelengths into one another.
Figure 6:
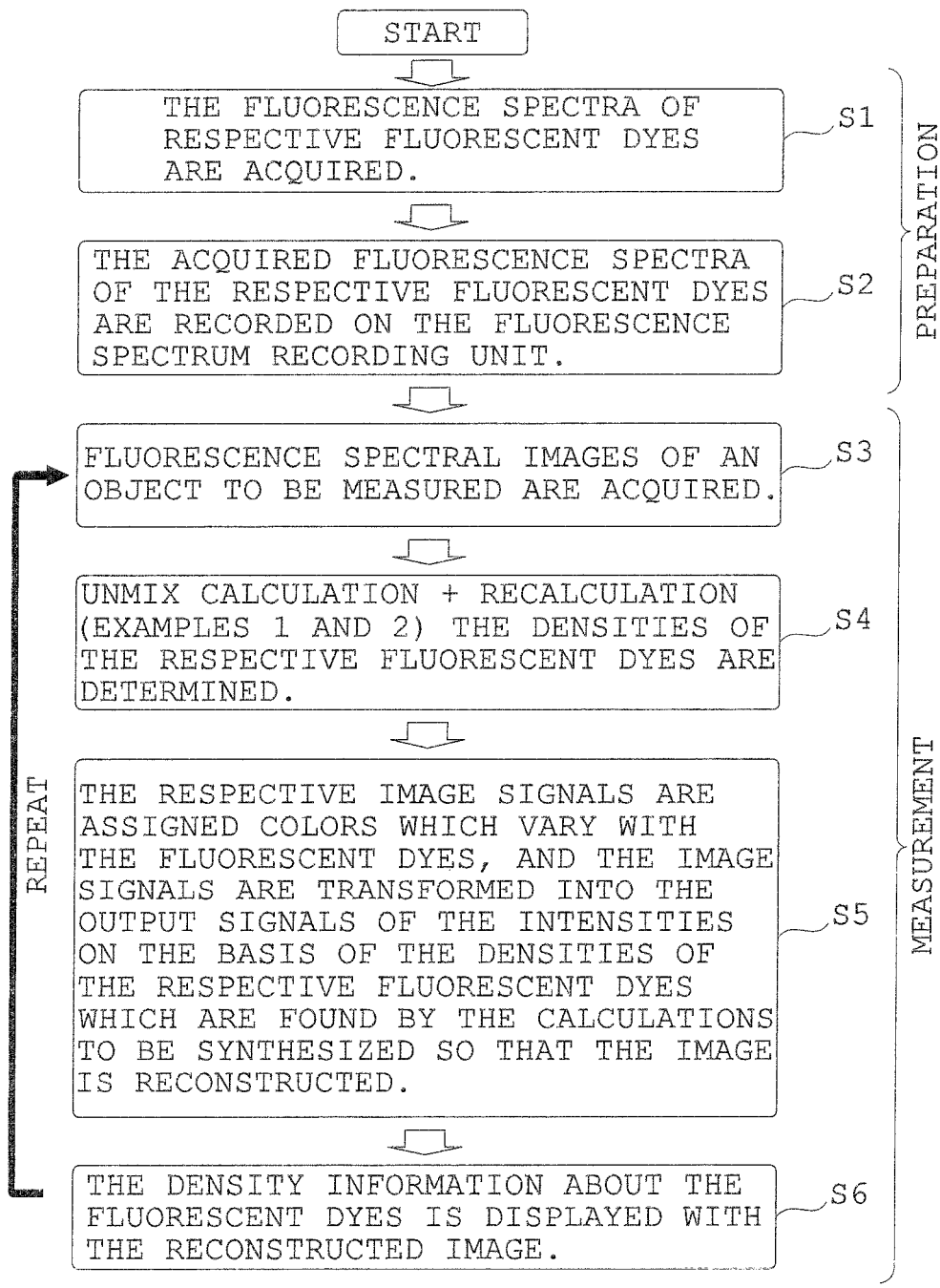
FIG. 6 is a flow chart showing a procedure for processing a fluorescence observation with the fluorescence endoscope apparatus shown in FIG. 5.

FIG. 4 is a block diagram showing a constitution of the whole of a fluorescence endoscope apparatus which is common to the examples of the present invention. FIG. 5 is a graph showing one example of optical characteristics in a fluorescence observation with the fluorescence endoscope apparatus shown in FIG. 4, FIG. 5A is a view showing the spectrum of excitation light, FIG. 5B is a view showing the spectral transmittance of an excitation light cut filter, FIG. 5C is a view showing an auto-fluorescence spectrum and the fluorescence spectrum of a fluorescent dye, and FIG. 5D is a view showing a range within which a spectral optical element that is used for the fluorescence endoscope apparatus shown in FIG. 6 repeatedly changes transmittable wavelengths into one another. FIG. 6 is a flow chart showing a procedure for processing a fluorescence observation with the fluorescence endoscope apparatus shown in FIG. 4.

The fluorescence endoscope apparatus which is shown in FIG. 4 includes a light source unit 1, an endoscope top end insertion unit 2, an image processing unit 3, and a display unit 4.

The light source unit 1 includes a light source and an excitation filter and is provided with a excitation-light source 11 which is formed in such a way that the excitation-light source 11 can emit light in the excitation wavelength range of 430 to 450 nm the central wavelength of which is a wavelength of 440 nm, as shown in FIG. 5A. Besides, in the endoscope system which is shown in FIG. 4, the light source unit 1 is also provided with a white-light source 12 and is connected to an illumination light change-controlling unit 13, so that the light source 1 can emit illumination light by switching one of excitation light from the excitation-light source 11 and white light from the white-light source 12 to the other through control by the illumination light change-controlling unit 13.

The endoscope top end insertion unit 2 includes an illumination optical system 21 and an image-pick up optical system 22.

The illumination optical system 21 radiates excitation light from the excitation-light source 11 through a light guide 23, to a biological tissue 5.

The biological tissue 5 contains a fluorescent dye (substance) 1 which emits auto-fluorescent light the peak wavelength of which is a wavelength of 460 nm and the wavelength of which is in the range of 440 to 650 nm, as shown in FIG. 5C, and the biological tissue 5 is labeled with a fluorescent probe which contains a fluorescent dye 2 which emits fluorescent light the peak wavelength of which is a wavelength of 520 nm and the wave length of which is in the range of 500 to 635 nm. In FIG. 4, the reference sign 5a denotes an area in the biological tissue 5 on which the fluorescent probes containing the fluorescent dye 2 accumulate.

The image-pick up optical system 22 includes an objective optical system 22a, an image-forming optical system 22b, an excitation light cut filter 22c, a spectral optical element 22e, and an image sensor 22d. In addition, a spectral optical element-controlling unit 22f is connected to the spectral optical element 22e and the image processing unit 3.

The excitation light cut filter 22c has an optical characteristic in which the excitation light cut filter 22c blocks light in the wavelength range of wavelengths of 450 nm or less, including excitation light, and transmits light in the wavelength range of 450 to 800 nm, as shown in FIG. 5B.

The spectral optical element 22e consists of an etalon and is controlled through the spectral optical element-controlling unit 22f so that the spectral optical element 22e can repeatedly make a change in a plurality of transmittable-wavelength states in which light in a set wavelength range is transmitted. In this case, as shown in FIG. 5D, the spectral optical element 22e switches from one of wavelengths λ1 of 450 to 480 nm with a peak wavelength of 470 nm and wavelengths λ2 of 510 to 530 nm with a peak wavelength of 520 nm into the other, to transmit light.

Etalons are such that interference of light is used for them and they can change the wavelength of light which can be transmitted or reflected by them by changing the distance between a pair of mirror planes that are arranged with the mirror planes facing each other.

The spectral optical element-controlling unit 22f controls the drive of the spectral optical element 22e, including a transmittable-wavelength state (transmittable wavelength range) of the spectral optical element 22e and a pitch at which the transmittable-wavelength states are changed into one another, together with timing of image processing by an image processing device 32 of the image processing unit 3, and the spectral optical element-controlling unit 22f is formed in such a way that the spectral optical element-controlling unit 22f makes the image processing device 32 perform image processing as often as the transmittable-wavelength states of the spectral optical element 22e are changed into one another.

The image sensor 22d is composed of a CCD which is provided with a single-chip image sensor (which is omitted in the drawings).

And, the image-pick up optical system 22 has a function as a fluorescence image acquiring unit for the present invention, through control by the spectral optical element-controlling unit 22f, and the image-pick up optical unit 22 is formed in such a way that a fluorescence image resulting from the biological tissue 5 can be acquired relative to each of two wavelength values λ1 and λ2 which are shown in FIG. 5D, by the image-pick up optical system 22.

The image processing unit 3 includes a frame memory 31, the image processing device 32, a fluorescence spectrum recording unit 33, and a fluorescent dye density-calculating unit 34.

Respective image signals which are acquired through the image-pick up optical system 22 are written onto the frame memory 31.

The respective image signals of the wavelengths λ1 and λ2 which are written on the frame memory 31 are synthesized by the image processing device 32, through control by the spectral optical element-controlling unit 22f (for example, as often as the image processing device 32 receives a command signal). In this case, in order to make it possible to easily distinguish a normal tissue region and a lesion tissue region, the image processing devise 32 assigns the respective image signals color phases which vary with fluorescent dye, and the image-processing device 32 transforms the respective image signals into the output signals of the intensities on the basis of the densities of the fluorescent dyes which are calculated by the fluorescent dye density-calculating unit 34.

The image which is processed through the image-processing devise 32 is displayed by the display unit 4.

The fluorescence spectra of two kinds of the respective fluorescent dyes 1 and 2 which are presumed to be present in the biological tissue 5 (refer to FIG. 5C), at the standard density, are recorded on the fluorescence spectrum recording unit 33.

When a1(λ1), a2(λ2) denote the coefficients for the respective fluorescent dyes 1 and 2 at the standard density at the respective wavelengths λ1 and λ2 respectively, which are obtained from the fluorescence spectra of the respective fluorescent dyes 1 and 2 at the standard density that are recorded on the fluorescence spectrum recording unit 1, $I_{all}(\lambda 1)$, $I_{all}(\lambda 2)$ denote the intensities of the fluorescence image acquired by the fluorescence image acquiring unit at the wavelengths λ1 and λ2, respectively, and D1 and D2 denote the densities of the fluorescent dyes 1 and 2, respectively, the fluorescent dye density-calculating unit 34 calculates the densities D1 and D2 of the fluorescent dyes 1 and 2 with the following equation (1). In this case, in the case where there exists a pixel in which one of the calculation values of the densities D1 and D2 of the fluorescent dyes 1 and 2 is smaller than 0, the fluorescent dye density-calculating unit 34 substitutes a set value which is larger than the value of the calculated density smaller than 0 for the density of a fluorescent dye the calculation value of which is smaller than 0 in the equation (1) and the density of the other fluorescent dye is recalculated, relative to the pixel:

$$\begin{pmatrix} D1 \\ D2 \end{pmatrix} = \begin{pmatrix} a1(\lambda 1) & a2(\lambda 1) \\ a1(\lambda 2) & a2(\lambda 2) \end{pmatrix}^{-1} \begin{pmatrix} I_{all}(\lambda 1) \\ I_{all}(\lambda 2) \end{pmatrix}. \quad \text{Equation (1)}$$

Next example 1 is different from next example 2 in recalculation process for the densities of specific fluorescent dyes by the fluorescent dye density-calculating unit 34 in the fluorescence endoscope apparatus which is shown in FIG. 4.

Example 1

Figure 7:
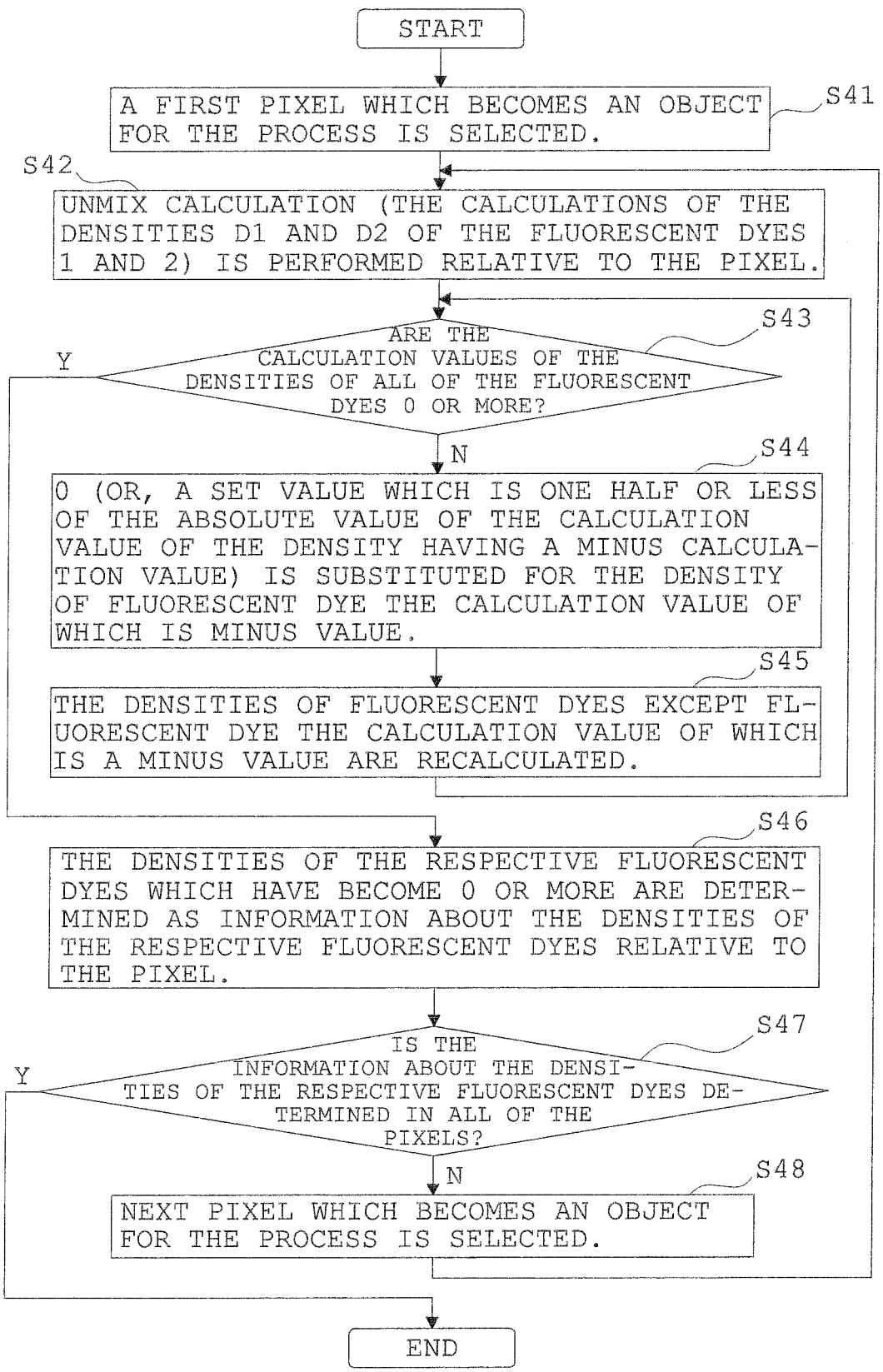
FIG. 7 is a flow chart showing a procedure for processing the UNMIX calculation and the recalculation which are shown in FIG. 6, and the determination of the density of each of fluorescent dyes in detail, as a primary part of the fluorescence endoscope apparatus of the embodiment 1.
Figure 8:
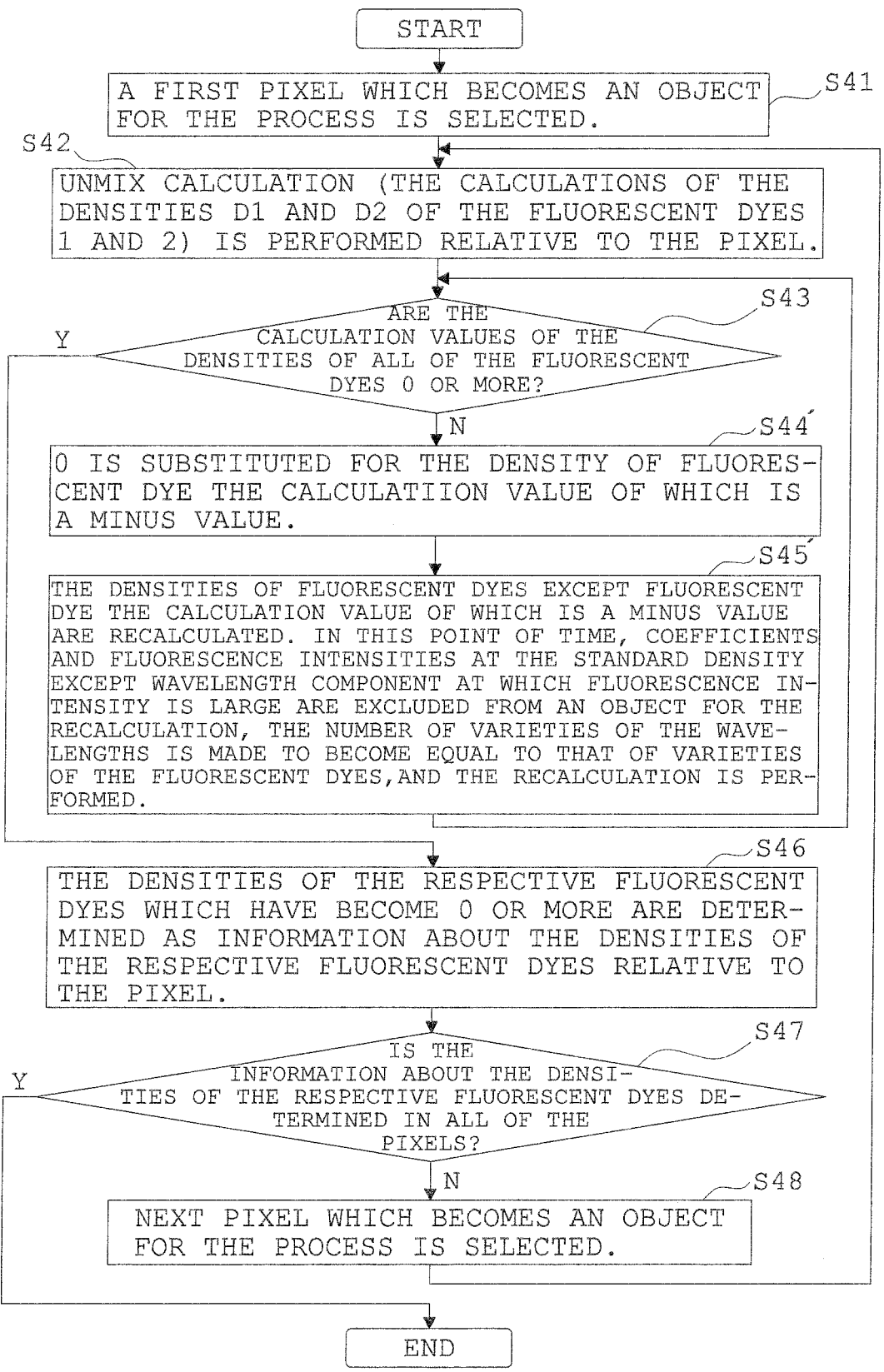
FIG. 8 is a flow chart showing a procedure for processing the UNMIX calculation and the recalculation which are shown in FIG. 6, and the determination of the density of each of fluorescent dyes in detail, as a primary part of the fluorescence endoscope apparatus of a variation of the example 1.

FIG. 7 is a flow chart showing a procedure for processing the UNMIX calculation and the recalculation which are shown in FIG. 6, and the determination of the density of each of fluorescent dyes in detail, as a primary part of the fluorescence endoscope apparatus of the example 1.

In the fluorescence endoscope apparatus of the example 1, the fluorescent dye density-calculating unit 34 has approximately the same constitution as those in the first and second embodiments. In the case where there exists a pixel in which one of the calculation values of the densities D1 and D2 of the fluorescent dyes 1 and 2 is smaller than 0, the fluorescence endoscope apparatus of the present embodiment is formed in such a way that the fluorescent dye density-calculating unit 34 substitutes 0 for the density of a fluorescent dye the calculation value of which is smaller than 0 (or, substitutes for the density of the fluorescent dye the calculation value of which is smaller than 0 a value approximating to 0, for example, a value which is one half or less of the absolute value of the calculation value of the density D2), in the equation (1) to recalculate the density of the other fluorescent dye, relative to the pixel.

Effects of the fluorescence endoscope apparatus of the example 1 are approximately the same as those of the fluorescence endoscope apparatus of the first and second embodiments.

Variation

FIG. 6 is a flow chart showing a procedure for processing the UNMIX calculation and the recalculation which are shown in FIG. 4, and the determination of the density of each of fluorescent dyes in detail, as a primary part of the fluorescence endoscope apparatus of a variation of the example 1.

In the fluorescence endoscope apparatus of a variation of the example 1, the fluorescent dye density-calculating unit 34 has approximately the same constitution as that in the fourth embodiment. The fluorescence endoscope apparatus of the variation of the example 1 is formed in such a way that, in the case where: there exists a pixel in which one of the calculation values of the densities D1 and D2 of the fluorescent dyes 1 and 2 is smaller than 0; 0 is substituted for the density of a fluorescent dye the calculation value of which is smaller than 0 in the equation (1), with respect to the pixel; and the density of fluorescent dye except fluorescent dye the calculation value of which is smaller than 0 is recalculated, coefficients and fluorescence intensities at the standard density at wavelengths except wavelength component at which fluorescence intensity of fluorescent dye the density of which is targeted at the recalculation is large are excluded from an object for the recalculation, the number of varieties of the wavelengths is made to become equal to that of varieties of the fluorescent dyes, and the recalculation is performed.

Effects of the fluorescence endoscope apparatus of the variation are approximately the same as those of the fluorescence endoscope apparatus of the fourth embodiment.

Example 2

Figure 9:
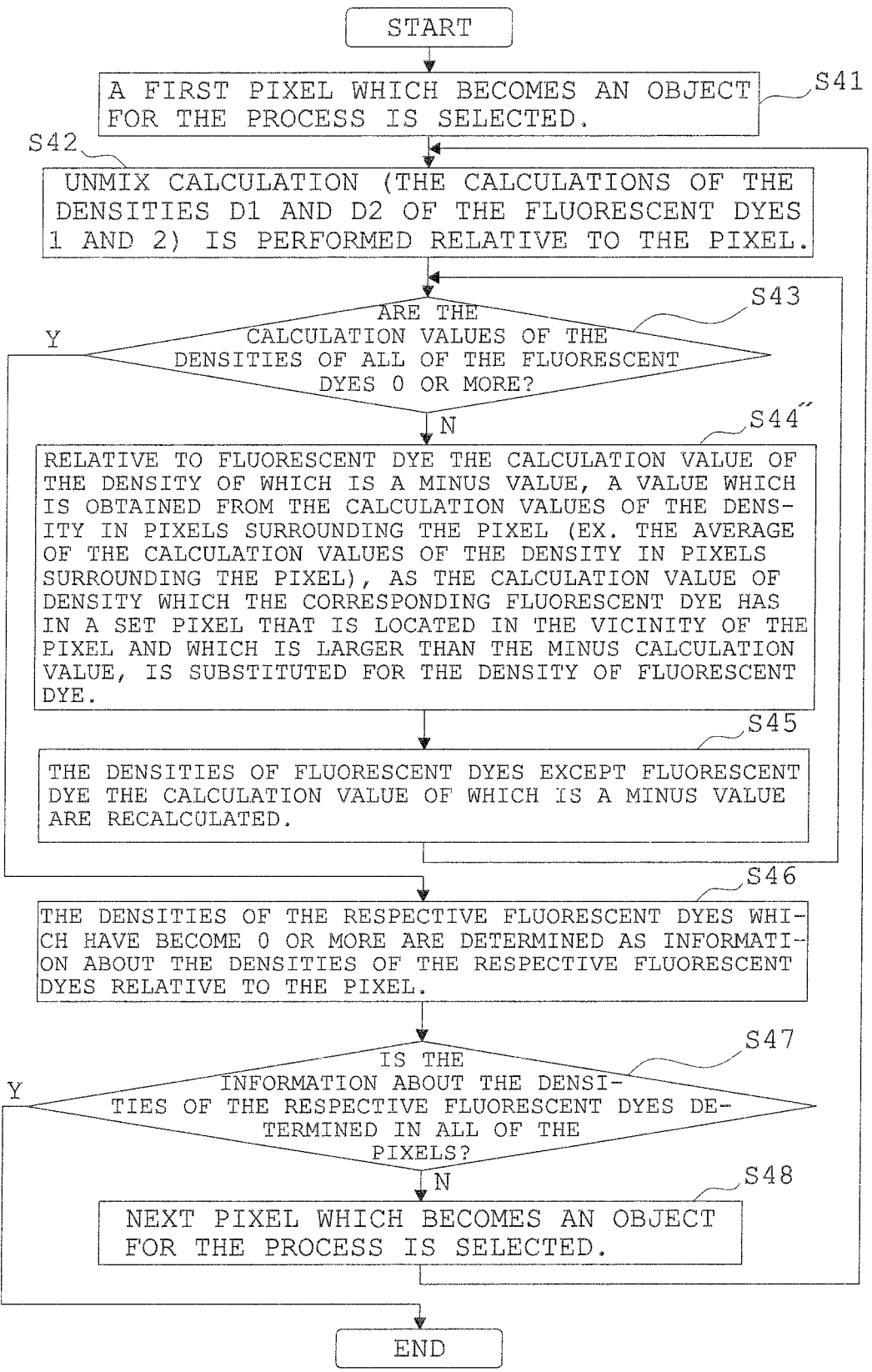
FIG. 9 is a flow chart showing a procedure for processing the UNMIX calculation and the recalculation which are shown in FIG. 6, and the determination of the density of each of fluorescent dyes in detail, as a primary part of the fluorescence endoscope apparatus of the example 2.

FIG. 9 is a flow chart showing a procedure for processing the UNMIX calculation and the recalculation which are shown in FIG. 6, and the determination of the density of each of fluorescent dyes in detail, as a primary part of the fluorescence endoscope apparatus of the example 2.

In the fluorescence endoscope apparatus of the example 2, the fluorescent dye density-calculating unit 34 has approximately the same constitution as that in the third embodiment. In the case where there exists a pixel in which one of the calculation values of the densities D1 and D2 of the fluorescent dyes 1 and 2 is smaller than 0, the fluorescence endoscope apparatus of the present embodiment is formed in such a way that the fluorescent dye density-calculating unit 34 substitutes for the density of a fluorescent dye the calculation value of which is smaller than 0 the calculation value of density which the corresponding fluorescent dye the calculation value of which is smaller than 0 in the pixel has in a set pixel that is located in the vicinity of the pixel and which is larger than the calculation value that is smaller than 0 [a value which is obtained from the calculation values of the density of the corresponding fluorescent dye in pixels surrounding the pixel (for example, the average of the calculation values of the density of the corresponding fluorescent dye in pixels surrounding the pixel)], in the equation (1) to perform recalculation, relative to the pixel.

Effects of the fluorescence endoscope apparatus of the example 2 are approximately the same as those of the fluorescence endoscope apparatus of the third embodiment.

A procedure for measuring multiplexed fluorescent lights with the fluorescence endoscope apparatuses of the examples 1 and 2 which are formed in such manners will be explained using FIG. 6.

A preparation process is first performed.

In the preparation process, for example, a solution for fluorescent dye is prepared for each of the fluorescent dyes 1 and 2 which are presumed to be present in the biological tissue 5, and a fluorescence spectrum is acquired with the fluorescence endoscope apparatus (step S1). In a detailed explanation of the step 1, the light source unit 1 emits excitation light from the excitation light source 11 through control by the illumination light change-controlling unit 13. The excitation light emitting from the light source unit 1 passes through the light guide 23 and is radiated from the illumination optical system 21 to the fluorescent dye 1 (or the fluorescent dye 2). Fluorescent light emitting from the fluorescent dye 1 (or the fluorescent dye 2) and excitation light reflected by the fluorescent dye 1 (or the fluorescent dye 2) passes through the objective optical system 22a and the image-forming optical system 22b, and then only the excitation light is blocked by the excitation light cut filter 22c and the fluorescent light enters the spectral optical element 22e. The spectral optical element 22e transmits light of the wavelength λ1 and light of the wavelength λ2 in the light incident on the spectral optical element 22e, one after the other. The image of the light transmitted by the spectral optical element 22e is captured by the image sensor 22d.

Next, the acquired fluorescence spectra of the respective fluorescent dyes are recorded on the fluorescence spectrum recording unit 33 in the image processing unit 3 (step S2). The signal intensities of the fluorescence spectra of the respective fluorescent dyes 1 and 2 at the respective wavelengths λ1 and λ2 which are recorded on the fluorescence spectrum recording unit 33 become density coefficients for the respective fluorescent dyes 1 and 2 at the standard density relative to the respective wavelengths λ1 and λ2.

Next, a process for measuring multiplexed fluorescent lights is performed.

In the process of measuring multiplexed fluorescent lights, a fluorescence image of the biological tissue 5 which contains the fluorescent dye 1 (or, auto-fluorescence) and is labeled with the fluorescent dye 2 (or, drug) is first acquired relative to each of two wavelength values λ1 and λ2 (step S3).

In a detailed explanation of the step 3, the light source unit 1 emits excitation light from the excitation light source 11 through control by the illumination light change-controlling unit 13. The excitation light emitting from the light source unit 1 passes through the light guide 23 and is radiated from the illumination optical system 21 to the biological tissue 5. Auto-fluorescent light of the fluorescent dye 1 emitting from the biological tissue 5, fluorescent light of the fluorescent dye 2 emitting from the biological tissue 5, and excitation light reflected by the biological tissue 5 pass through the objective optical system 22a and the image-forming optical system 22b, and then only the excitation light is blocked by the excitation light cut filter 22c and the auto-fluorescent light and the fluorescent light enter the spectral optical element 22e. The spectral optical element 22e transmits light of the wavelength λ1 and light of the wavelength λ2 in the light incident on the spectral optical element 22e, one after the other. The image of the light transmitted by the spectral optical element 22e is captured by the image sensor 22d. The acquired fluorescence image is written on the frame memory 31.

Next, the fluorescent dye density-calculating unit 34 calculates the densities D1 and D2 of the respective fluorescent dyes 1 and 2 which are present in the biological tissue 5 with the equation (1) relative to all of the pixels in the fluorescence images, with two kinds of the fluorescence spectral images which are acquired by the fluorescence image acquiring unit (the image-pick up optical system 22, the spectral optical element-controlling unit 22f) to be written on the frame memory 31, the fluorescence spectra of the respective fluorescent dyes 1 and 2 at the standard density which are recorded on the fluorescence spectrum recording unit 33, and the spectral images relative to respective two wavelength values λ1 and λ2 which are acquired by the fluorescence image acquiring unit.

In this case, in the case where there exists a pixel in which one of the calculation values of the densities D1 and D2 of the fluorescent dyes 1 and 2 is smaller than 0, the fluorescent dye density-calculating unit 34 substitutes a set value which is larger than the calculation value smaller than 0 for the density of a fluorescent dye the calculation value of which is smaller than 0 in the following equation (1) and the density of the other fluorescent dye is recalculated, relative to the pixel:

$$\begin{pmatrix} D1 \\ D2 \end{pmatrix} = \begin{pmatrix} a1(\lambda 1) & a2(\lambda 1) \\ a1(\lambda 2) & a2(\lambda 2) \end{pmatrix}^{-1} \begin{pmatrix} I_{all}(\lambda 1) \\ I_{all}(\lambda 2) \end{pmatrix}. \quad (1)$$

Through these calculation and recalculation, the densities of the fluorescent dyes 1 and 2 are found (step S4).

Now, procedures for processing the step S4 in the respective embodiments will be explained in detail.

Example 1

In the fluorescence endoscope apparatus of the example 1, the fluorescent dye density-calculating unit 34 selects a first pixel which becomes an object for the process (step S41).

Next, UNMIX calculation (the calculations of the densities D1 and D2 of the fluorescent dyes 1 and 2) is performed relative to the pixel (step S42). In the case where there exists a pixel in which one of the densities D1 and D2 of the fluorescent dyes 1 and 2 is smaller than 0 (step S43), relative to the pixel, the fluorescent dye density-calculating unit 34 substitutes 0 for the density of a fluorescent dye the calculation value of which is smaller than 0 (or, substitutes for the density of the fluorescent dye the calculation value of which is smaller than 0 a value approximating to 0, for example, a value which is one half or less of the absolute value of the calculation value of the density D2), in the equation (1) (step S44), and the fluorescence dye density-calculating unit 34 recalculates the density of the other fluorescent dye (step S45). When the calculation values of the densities of all of the fluorescent dyes are 0 or more in the pixel (step S43), the densities of the respective fluorescent dyes which have become 0 or more are determined as information about the densities of the respective fluorescent dyes relative to the pixel (step S46). All of the processes of these steps S42 to S46 are performed relative to all of the pixels (step S47, step S48).

Variation of Example 1

In the fluorescence endoscope apparatus of the variation of the example 1, the fluorescent dye density-calculating unit 34 selects a first pixel which becomes an object for the process (step S41). Next, UNMIX calculation (the calculations of the densities D1 and D2 of the fluorescent dyes 1 and 2) is performed relative to the pixel (step S42). In the case where there exists a pixel in which one of the densities D1 and D2 of the fluorescent dyes 1 and 2 is smaller than 0 (step S43), relative to the pixel, the fluorescent dye density-calculating unit 34 substitutes 0 for the density of a fluorescent dye the calculation value of which is smaller than 0 in the equation (1) (step S44'), and the fluorescence dye density-calculating unit 34 recalculates the density of the other fluorescent dye. In this point of time, coefficients and fluorescence intensities at the standard density except wavelength component at which fluorescence intensity is large are excluded from an object for the recalculation, the number of varieties of the wavelengths is made to become equal to that of varieties of the fluorescent dyes, and the recalculation is performed (step S45'). When the calculation values of the densities of all of the fluorescent dyes are 0 or more in the pixel (step S43), the densities of the respective fluorescent dyes which have become 0 or more are determined as information about the densities of the respective fluorescent dyes relative to the pixel (step S46). All of the processes of these steps S42 to S46 are performed relative to all of the pixels (step S47, step S48).

Example 2

In the fluorescence endoscope of the example 2, the fluorescent dye density-calculating unit 34 selects a first pixel which becomes an object for the process (step S41). Next, UNMIX calculation (the calculations of the densities D1 and D2 of the fluorescent dyes 1 and 2) is performed relative to the pixel (step S42). In the case where there exists a pixel in which one of the densities D1 and D2 of the fluorescent dyes 1 and 2 is smaller than 0 (step S43), relative to the pixel, the fluorescence dye density-calculating unit 34 substitutes for the density of a fluorescent dye the calculation value of which is smaller than 0 a value which is obtained from the calculation values of the density of the corresponding fluorescent dye in pixels surrounding the pixel (for example, the average of the calculation values of the density of the corresponding fluorescent dye in pixels surrounding the pixel), as the calculation value of density which the corresponding fluorescent dye the calculation value of which is smaller than 0 in the pixel has in a set pixel that is located in the vicinity of the pixel and which is larger than the calculation value that is smaller than 0, in the equation (1) (step S44''), and the fluorescence dye density-calculating unit 34 recalculates the density of the other fluorescent dye (step S45). When the calculation values of the densities of all of the fluorescent dyes are 0 or more in the pixel (step S43), the densities of the respective fluorescent dyes which have become 0 or more are determined as information about the densities of the respective fluorescent dyes relative to the pixel (step S46). All of the processes of these steps S42 to S46 are performed relative to all of the pixels (step S47, step S48).

Next, the image processing devise 32 assigns the image signals at the respective wavelengths $\lambda 1$ and $\lambda 2$ color phases which vary with the fluorescent dyes 1 and 2, respectively (for example, red to the fluorescent dye 1 and green to the fluorescent dye 2). And, the image-processing device 32 transforms the image signals into the output signals of the intensities on the basis of the densities D1 and D2 of the fluorescent dyes 1 and 2 which are found by the calculation with the equation (1), and then the transformed image signals are synthesized by the image processing device 32. As a result, the image of the biological tissue is reconstructed with the image distinguished by using different colors depending on fluorescent dye. Besides, the image processing unit 32 may transform the image signals at the respective wavelengths 1 and 2 into the output signals of the intensities on the basis of the density relative to each of the fluorescent dyes 1 and 2 individually to synthesize the transformed image signals so that the image is reconstructed (step S5).

Next, the display unit 4 displays the reconstructed image in such a way that the fluorescence density image information about respective two kinds of the fluorescent dyes 1 and 2 is distinguished by using different colors, or displays the reconstructed image relative to the fluorescence density image information about each one kind of fluorescent dye separately from the other kinds of fluorescent dyes (step S6).

The processes of these steps S3 to S6 are repeatedly performed until the observation of the biological tissue 5 is finished.

Besides, of course, it is also possible to perform another observation other than the above-described observation of multiplexed fluorescent lights with the fluorescence endoscope apparatuses of the examples 1 and 2.

For example, when the light source unit 1 is switched through control by the illumination light change-controlling unit 13 to emits white light from the white-light source 12, the white light is radiated to the biological tissue 5, reflection light from the biological tissue 5 is acquired through the image-pick up optical system 22 excluding light of a part of the wavelength range, a color image is synthesized through the image processing unit 32, and the synthesized color image is displayed by the display unit 4. As a result, it is possible to perform a reflection image observation in color with usual white light.

Also, for example, in the fluorescence observation, when the spectral optical element 22e is controlled through the spectral optical element-controlling unit 22f in such a way that the spectral optical element 22e transmits only light in one wavelength range, a fluorescence image relative to wavelength range is acquired and the fluorescence image is displayed by the display unit 4. As a result, it is possible to perform a fluorescence image observation relative to one wavelength range.

Also, for example, in performing the fluorescence observation with more than one wavelength, when the image processing unit 32 synthesizes the respective image signals at the wavelengths $\lambda 1$ and $\lambda 2$ which are written on the frame memory 31, through control by the spectral optical element-controlling unit 22f, the respective image signals are assigned color phases which vary with the image signals.

As a result, it is possible to perform a fluorescence image observation with the fluorescence image distinguished by using different colors depending on wavelength.

Up to now, the embodiments and examples of fluorescence endoscope apparatus of the present invention were explained. However, fluorescence endoscope apparatuses of the present invention are not limited to these embodiments and examples, and fluorescence endoscope apparatuses of the present invention may be formed by combining characteristic constitutions of the respective embodiments and examples.

Also, it is better to form fluorescence endoscope apparatuses of the present invention in such a way that: desired kinds of fluorescent dyes can be set through selection screen input or the like, in accordance with varieties of fluorescent dyes which vary with biological tissue to be observed, the aim of observation, observation condition, and so on; the fluorescence spectrum recording unit 33 is provided with fluorescence spectra of many kinds of fluorescent dyes at the standard density; and it is possible to calculate the densities of the desired fluorescent dyes which are set through selection screen input or the like, by the fluorescent dye density-calculating unit 34.

A fluorescence endoscope apparatus of the present invention is useful for a fluorescence endoscope apparatus in which excitation light is radiated to a biological tissue and a lesion in the biological tissue is observed through fluorescent light emitting from the biological tissue.

What is claimed is:
1. A fluorescence endoscope apparatus in which excitation light is radiated to a biological tissue and a lesion in the biological tissue is observed with fluorescent light that emits from the biological tissue, comprising:
   a memory on which the respective fluorescence spectra of m kinds (where, $2 \leq m$) of fluorescent dyes 1 to m that are presumed to be present in the biological tissue, at a standard density, are recorded;
   an image sensor by which a fluorescence image resulting from the biological tissue is acquired relative to each of n (where, $m \leq n$) wavelength values $\lambda 1$ to $\lambda n$; and
   a processor comprising hardware, by which the densities of the respective fluorescent dyes that are present in the biological tissue are calculated to be found in each of all the pixels in each of the fluorescence images, with the respective fluorescence spectra of the m kinds of the fluorescent dyes 1 to m at the standard density which are recorded on the memory and the fluorescence images relative to the respective n wavelength values $\lambda 1$ to $\lambda n$ which are acquired by the image sensor,
   wherein, when $a1(\lambda 1)$ to $am(\lambda n)$ denote the coefficients for the respective fluorescent dyes 1 to m at the standard density at the respective wavelengths $\lambda 1$ to $\lambda n$ respectively, which are obtained from the fluorescence spectra of the respective fluorescent dyes 1 to m at the standard density that are recorded on the memory,

$I_{all}(\lambda 1)$ to $I_{all}(\lambda n)$ denote the intensities of the fluorescence image acquired by the image sensor at the wavelengths $\lambda 1$ to $\lambda n$, respectively, and D1 to Dm denote the densities of the respective fluorescent dyes 1 to m, the processor calculates the densities D1 to Dm of the fluorescent dyes 1 to m in each of all the pixels in the fluorescence images and in all of the pixels with the following equation (1"), and wherein in the case where there exists a pixel in which at least one of the calculation values of the densities D1 to Dm of the fluorescent dyes 1 to m is smaller than 0, the processor substitutes a set value which is larger than the calculation value smaller than 0 for the density of a fluorescent dye the calculation value of which is smaller than 0 in the equation (1") and the densities of fluorescent dyes except fluorescent dye the calculation value of which is smaller than 0 are recalculated, relative to the pixel:

$$\begin{pmatrix} D1 \\ \vdots \\ Dm \end{pmatrix} = \begin{pmatrix} a1(\lambda 1) & \cdots & am(\lambda 1) \\ \vdots & \vdots & \vdots \\ a1(\lambda n) & \cdots & am(\lambda n) \end{pmatrix}^{-1} \begin{pmatrix} I_{all}(\lambda 1) \\ \vdots \\ I_{all}(\lambda n) \end{pmatrix}. \quad (1'')$$

2. A fluorescence endoscope apparatus according to claim 1, wherein, in the case where there exists a pixel in which at least one of the calculation values of the densities D1 to Dm of the fluorescent dyes 1 to m is smaller than 0, the processor substitutes a set value the absolute value of which is smaller than that of the calculation value smaller than 0 for the density of fluorescent dye the calculation value of which is smaller than 0 in the equation (1") and the densities of fluorescent dyes except fluorescent dye the calculation value of which is smaller than 0 are recalculated, relative to the pixel.

3. A fluorescence endoscope apparatus according to claim 1, wherein, in the case where there exists a pixel in which at least one of the calculation values of the densities D1 to Dm of the fluorescent dyes 1 to m is smaller than 0, the processor substitutes a set value the absolute value of which is one-half or less of the absolute value of the calculation value smaller than 0 for the density of fluorescent dye the calculation value of which is smaller than 0 in the equation (1") and the densities of fluorescent dyes except fluorescent dye the calculation value of which is smaller than 0 are recalculated, relative to the pixel.

4. A fluorescence endoscope apparatus according to one of claim 1, wherein, in the case where the densities of fluorescent dyes except fluorescent dye the calculation value of which is smaller than 0 are recalculated, in the equation (1"), and wherein in the coefficients $a1(\lambda 1)$ to $am(\lambda n)$ for the respective fluorescent dyes 1 to m at the standard density at the respective wavelengths $\lambda 1$ to $\lambda n$ and the intensities $I_{all}(\lambda 1)$ to $I_{all}(\lambda n)$ of the fluorescence image acquired by the image sensor at the respective wavelengths $\lambda 1$ to $\lambda n$, coefficients and fluorescence intensities at the standard density at wavelengths except wavelength component at which fluorescence intensity of fluorescent dye the density of which is targeted at the recalculation are excluded from an object for the recalculation, the number of varieties of the wavelengths is made to become equal to that of varieties of the fluorescent dyes, and the recalculation is performed.

5. A fluorescence endoscope apparatus according to claim 1, wherein, in the case where there exists a pixel in which at least one of the calculation values of the densities D1 to Dm of the fluorescent dyes 1 to m is smaller than 0, the processor substitutes 0 for the density of fluorescent dye the calculation value of which is smaller than 0 in the equation (1") and the densities of fluorescent dyes except fluorescent dye the calculation value of which is smaller than 0 are recalculated, relative to the pixel.

6. A fluorescence endoscope apparatus according to one of claim 5, wherein, in the case where the densities of fluorescent dyes except fluorescent dye the calculation value of which is smaller than 0 are recalculated, in the equation (1"), and wherein in the coefficients $a1(\lambda 1)$ to $am(\lambda n)$ for the respective fluorescent dyes 1 to m at the standard density at the respective wavelengths $\lambda 1$ to $\lambda n$ and the intensities $I_{all}(\lambda 1)$ to $I_{all}(\lambda n)$ of the fluorescence image acquired by the image sensor at the respective wavelengths $\lambda 1$ to $\lambda n$, at the standard density at wavelengths except wavelength component at which fluorescence intensity of fluorescent dye the density of which is targeted at the recalculation are excluded from an object for the recalculation, the number of varieties of the wavelengths is made to become equal to that of varieties of the fluorescent dyes, and the recalculation is performed.

7. A fluorescence endoscope apparatus according to claim 1, wherein in the case where there exists a pixel in which at least one of the calculation values of the densities D1 to Dm of the fluorescent dyes 1 to m is smaller than 0, the processor substitutes for the density of fluorescent dye the calculation value of which is smaller than 0 the calculation value of density which the corresponding fluorescent dye has in a set pixel that is located in the vicinity of the pixel and which is larger than the calculation value that is smaller than 0, in the equation (1"), and the densities of fluorescent dyes except fluorescent dye the calculation value of which is smaller than 0 are recalculated, relative to the pixel.

8. A fluorescence endoscope apparatus according to one of claim 7, wherein, in the case where the densities of fluorescent dyes except fluorescent dye the calculation value of which is smaller than 0 are recalculated, in the equation (1"), wherein in the coefficients $a1(\lambda 1)$ to $am(\lambda n)$ for the respective fluorescent dyes 1 to m at the standard density at the respective wavelengths $\lambda 1$ to $\lambda n$ and the intensities $I_{all}(\lambda 1)$ to $I_{all}(\lambda n)$ of the fluorescence image acquired by the image sensor at the respective wavelengths $\lambda 1$ to $\lambda n$, coefficients and fluorescence intensities at the standard density at wavelengths except wavelength component at which fluorescence intensity of fluorescent dye the density of which is targeted at the recalculation are excluded from an object for the recalculation, the number of varieties of the wavelengths is made to become equal to that of varieties of the fluorescent dyes, and the recalculation is performed.

9. A fluorescence endoscope apparatus in which excitation light is radiated to a biological tissue and a lesion in the biological tissue is observed with fluorescent light that emits from the biological tissue, comprising:

a memory on which the respective fluorescence spectra of two kinds of fluorescent dyes 1 and 2 that are presumed to be present in the biological tissue, at the standard density, are recorded;

an image sensor by which a fluorescence image resulting from the biological tissue is acquired relative to each of two wavelength values λ1 and λ2; and a processor comprising hardware, by which the densities of the respective fluorescent dyes that are present in the biological tissue are calculated to be found in each of all the pixels in each of the fluorescence images, with the respective fluorescence spectra of the two kinds of the fluorescent dyes 1 and 2 at the standard density which are recorded on the memory and the fluorescence images relative to the respective two wavelength values λ1 and λ2 which are acquired by the image sensor, wherein, when a1(λ1) denotes the coefficient for the fluorescent dye 1 at the standard density at the wavelength λ1, which is obtained from the fluorescence spectra of the respective fluorescent dyes 1 and 2 at the standard density that are recorded on the memory, a1(λ2) denotes the coefficient for the fluorescent dye 1 at the standard density at the wavelength λ2, which is obtained from the fluorescence spectra of the respective fluorescent dyes 1 and 2 at the standard density that are recorded on the memory, a2(λ1) denotes the coefficient for the fluorescent dye 2 at the standard density at the wavelength λ1, which is obtained from the fluorescence spectra of the respective fluorescent dyes 1 and 2 at the standard density that are recorded on the memory, a2(λ2) denotes the coefficient for the fluorescent dye 2 at the standard density at the wavelength λ2, which is obtained from the fluorescence spectra of the respective fluorescent dyes 1 and 2 at the standard density that are recorded on the memory, $I_{all}(\lambda 1)$ denotes the intensity of the fluorescence image acquired by the image sensor at the wavelength λ1, $I_{all}(\lambda 2)$ denotes the intensity of the fluorescence image acquired by the image sensor at the wavelength λ2, D1 denotes the density of the fluorescent dye 1, and D2 denotes the density of the fluorescent dye 2, wherein the processor calculates the densities D1 and D2 of the fluorescent dyes 1 and 2 in each of all the pixels in the fluorescence images and in all of the pixels with the following equation (1), and wherein in the case where there exists a pixel in which one of the calculation values of the densities D1 and D2 of the fluorescent dyes 1 and 2 is smaller than 0, the processor substitutes a set value which is larger than the calculation value smaller than 0 for the density of fluorescent dye the calculation value of which is smaller than 0 in the equation (1) and the density of the other fluorescent dye is recalculated, relative to the pixel:

$$\begin{pmatrix} D1 \\ D2 \end{pmatrix} = \begin{pmatrix} a1(\lambda 1) & a2(\lambda 1) \\ a1(\lambda 2) & a2(\lambda 2) \end{pmatrix}^{-1} \begin{pmatrix} I_{all}(\lambda 1) \\ I_{all}(\lambda 2) \end{pmatrix}. \quad (1)$$

10. A fluorescence endoscope apparatus according to claim 9, wherein, in the case where there exists a pixel in which one of the calculation values of the densities D1 and D2 of the fluorescent dyes 1 and 2 is smaller than 0, the processor substitutes 0 for the density of fluorescent dye the calculation value of which is smaller than 0 in the equation (1) and the density of the other fluorescent dye is recalculated, relative to the pixel.

11. A fluorescence endo scope apparatus according to claim 9, wherein, in the case where there exists a pixel in which one of the calculation values of the densities D1 and D2 of the fluorescent dyes 1 and 2 is smaller than 0, the processor substitutes a set value the absolute value of which is smaller than that of the calculation value smaller than 0 for the density of fluorescent dye the calculation value of which is smaller than 0 in the equation (1) and the density of the other fluorescent dye is recalculated, relative to the pixel.

12. A fluorescence endoscope apparatus according to claim 9, wherein, in the case where there exists a pixel in which one of the calculation values of the densities D1 and D2 of the fluorescent dyes 1 and 2 is smaller than 0, the processor substitutes a set value the absolute value of which is one-half or less of the absolute value of the calculation value smaller than 0 for the density of fluorescent dye the calculation value of which is smaller than 0 in the equation (1) and the density of the other fluorescent dye is recalculated, relative to the pixel.

13. A fluorescence endoscope apparatus according to claim 9, wherein, in the case where there exists a pixel in which one of the calculation values of the densities D1 and D2 of the fluorescent dyes 1 and 2 is smaller than 0, the processor substitutes for the density of fluorescent dye the calculation value of which is smaller than 0 the calculation value of density which the corresponding fluorescent dye has in a set pixel that is located in the vicinity of the pixel and which is larger than the calculation value that is smaller than 0, in the equation (1), and the density of the other fluorescent dye is recalculated, relative to the pixel.

14. A fluorescence endoscope apparatus in which excitation light is radiated to a biological tissue and a lesion in the biological tissue is observed with fluorescent light that emits from the biological tissue, comprising:

a memory on which the respective fluorescence spectra of three kinds of fluorescent dyes 1 to 3 that are presumed to be present in the biological tissue, at the standard density, are recorded;

an image sensor by which a fluorescence image resulting from the biological tissue is acquired relative to each of three wavelength values λ1 to λ3; and a processor comprising hardware, by which the densities of the respective fluorescent dyes that are present in the biological tissue are calculated to be found in each of all the pixels in the fluorescence images, with the respective fluorescence spectra of the three kinds of the fluorescent dyes 1 to 3 at the standard density which are recorded on the memory and the fluorescence images relative to the respective three wavelength values λ1 to λ3 which are acquired by the image sensor, wherein, when a1(λ1) denotes the coefficient for the fluorescent dye 1 at the standard density at the wavelength λ1, which is obtained from the fluorescence spectra of the respective fluorescent dyes 1 to 3 at the standard density that are recorded on the memory, a1(λ2) denotes the coefficient for the fluorescent dye 1 at the standard density at the wavelength 2, which is obtained from the fluorescence spectra of the respective fluorescent dyes 1 to 3 at the standard density that are recorded on the memory, a1(λ3) denotes the coefficient for the fluorescent dye 1 at the standard density at the wavelength λ3, which is obtained from the fluorescence spectra of the respective fluorescent dyes 1 to 3 at the standard density that are recorded on the memory, a2(λ1) denotes the coefficient for the fluorescent dye 2 at the standard density at the wavelength λ1, which is obtained from the fluorescence spectra of the respective fluorescent dyes 1 to 3 at the standard density that are recorded on the memory, a2(λ2) denotes the coefficient for the fluorescent dye 2 at the standard density at the wavelength λ2, which is obtained from the fluorescence spectra of the respective fluorescent dyes 1 to 3 at the standard density that are recorded on the memory, a2(λ3) denotes the coefficient for the fluorescent dye 2 at the standard density at the wavelength λ3, which is obtained from the fluorescence spectra of the respective fluorescent dyes 1 to 3 at the standard density that are recorded on the memory, a3(λ1) denotes the coefficient for the fluorescent dye 3 at the standard density at the wavelength λ1, which is obtained from the fluorescence spectra of the respective fluorescent dyes 1 to 3 at the standard density that are recorded on the memory, a3(λ2) denotes the coefficient for the fluorescent dye 3 at the standard density at the wavelength λ2, which is obtained from the fluorescence spectra of the respective fluorescent dyes 1 to 3 at the standard density that are recorded on the memory, a3(λ3) denotes the coefficient for the fluorescent dye 3 at the standard density at the wavelength λ3, which is obtained from the fluorescence spectra of the respective fluorescent dyes 1 to 3 at the standard density that are recorded on the memory, $I_{all}(\lambda 1)$ denotes the intensity of the fluorescence image acquired by the image sensor at the wavelength $\lambda_1$, $I_{all}(\lambda 2)$ denotes the intensity of the fluorescence image acquired by the fluorescence image acquiring unit at the wavelength λ2, $I_{all}(\lambda 3)$ denotes the intensity of the fluorescence image acquired by the image sensor at the wavelength λ3, D1 denotes the density of the fluorescent dye 1, D2 denotes the density of the fluorescent dye 2, and D3 denotes the density of the fluorescent dye 3, wherein the processor calculates the densities D1 to D3 of the fluorescent dyes 1 to 3 in each of all the pixels in the fluorescence image and in all of the pixels with the following equation (1'), and wherein in the case where there exists a pixel in which at least one of the calculation values of the densities D1 to D3 of the fluorescent dyes 1 to 3 is smaller than 0, the processor substitutes a set value which is larger than the calculation value smaller than 0 for the density of fluorescent dye the calculation value of which is smaller than 0 in the equation (1') and the densities of fluorescent dyes except fluorescent dye the calculation value of which is smaller than 0 are recalculated, relative to the pixel:

$$\begin{pmatrix} D1 \\ D2 \\ D3 \end{pmatrix} = \begin{pmatrix} a1(\lambda 1) & a2(\lambda 1) & a3(\lambda 1) \\ a1(\lambda 2) & a2(\lambda 2) & a3(\lambda 2) \\ a1(\lambda 3) & a2(\lambda 3) & a3(\lambda 3) \end{pmatrix}^{-1} \begin{pmatrix} I_{all}(\lambda 1) \\ I_{all}(\lambda 2) \\ I_{all}(\lambda 3) \end{pmatrix}. \qquad (1')$$

15. A fluorescence endoscope apparatus according to claim 14, wherein, in the case where there exists a pixel in which at least one of the calculation values of the densities D1 to D3 of the fluorescent dyes 1 to 3 is smaller than 0, the processor substitutes 0 for the density of fluorescent dye the calculation value of which is smaller than 0 in the equation (1') and the densities of fluorescent dyes except fluorescent dye the calculation value of which is smaller than 0 are recalculated, relative to the pixel.

16. A fluorescence endoscope apparatus according to claim 14, wherein, in the case where there exists a pixel in which at least one of the calculation values of the densities D1 to D3 of the fluorescent dyes 1 to 3 is smaller than 0, the processor substitutes a set value the absolute value of which is smaller than that of the calculation value smaller than 0 for the density of fluorescent dye the calculation value of which is smaller than 0 in the equation (1') and the densities of fluorescent dyes except fluorescent dye the calculation value of which is smaller than 0 are recalculated, relative to the pixel.

17. A fluorescence endoscope apparatus according to claim 14, wherein, in the case where there exists a pixel in which at least one of the calculation values of the densities D1 to D3 of the fluorescent dyes 1 to 3 is smaller than 0, the processor substitutes a set value the absolute value of which is one-half or less of the absolute value of the calculation value smaller than 0 for the density of fluorescent dye the calculation value of which is smaller than 0 in the equation (1') and the densities of fluorescent dyes except fluorescent dye the calculation value of which is smaller than 0 are recalculated, relative to the pixel.

18. A fluorescence endoscope apparatus according to claim 14, wherein, in the case where there exists a pixel in which at least one of the calculation values of the densities D1 to D3 of the fluorescent dyes 1 to 3 is smaller than 0, the processor substitutes for the density of fluorescent dye the calculation value of which is smaller than 0 the calculation value of density which the corresponding fluorescent dye has in a set pixel that is located in the vicinity of the pixel and which is larger than the calculation value that is smaller than 0, in the equation (1'), and the densities of fluorescent dyes except fluorescent dye the calculation value of which is smaller than 0 are recalculated, relative to the pixel.

\* \* \* \* \*

UNITED STATES PATENT AND TRADEMARK OFFICE
CERTIFICATE OF CORRECTION

| | |
|---|---|
| PATENT NO. | : 9,521,947 B2 |
| APPLICATION NO. | : 13/611826 |
| DATED | : December 20, 2016 |
| INVENTOR(S) | : Koki Morishita |

It is certified that error appears in the above-identified patent and that said Letters Patent is hereby corrected as shown below:

Column 26, Line 61 (Claim 14, Line 27):
Should read: at the standard density at the wavelength λ2, which is Signed and Sealed this
Fifteenth Day of August, 2017

Joseph Matal
*Performing the Functions and Duties of the
Under Secretary of Commerce for Intellectual Property and
Director of the United States Patent and Trademark Office*